US007109160B1

(12) United States Patent
Schor

(10) Patent No.: US 7,109,160 B1
(45) Date of Patent: Sep. 19, 2006

(54) PEPTIDES CONTAINING THE MOTIF IGD AND THEIR USE AS CELL MIGRATION MODULATORS

(75) Inventor: Seth Lawrence Schor, Dundee (GB)

(73) Assignee: University of Dundee, Dundee (GB)

( * ) Notice: Subject to any disclaimer, the term of this patent is extended or adjusted under 35 U.S.C. 154(b) by 0 days.

(21) Appl. No.: 09/446,274

(22) PCT Filed: Jul. 1, 1998

(86) PCT No.: PCT/GB98/01939

§ 371 (c)(1),
(2), (4) Date: Apr. 10, 2000

(87) PCT Pub. No.: WO99/02674

PCT Pub. Date: Jan. 21, 1999

(30) Foreign Application Priority Data

Jul. 8, 1997 (GB) ................... 9714276.4

(51) Int. Cl.
*A61K 38/00* (2006.01)
(52) U.S. Cl. ................... 514/2; 514/18; 530/330; 530/331
(58) Field of Classification Search ............. 514/2, 514/18, 17, 16, 15, 14; 530/300, 330, 331, 530/329, 328
See application file for complete search history.

(56) References Cited

U.S. PATENT DOCUMENTS

| | | | |
|---|---|---|---|
| 4,976,734 A | 12/1990 | Urry et al. ................... 2/2 |
| 4,980,279 A | 12/1990 | Peters et al. ................. 33/53 |
| 5,049,658 A | 9/1991 | Kimizuka et al. | |
| 5,124,155 A | 6/1992 | Reich ........................ 9/70 |
| 5,192,746 A | 3/1993 | Lobl et al. .................. 37/2 |
| 5,300,630 A | 4/1994 | Matsuura et al. .............. 37/2 |
| 5,354,736 A | 10/1994 | Bhatnagar | |
| 5,453,489 A | 9/1995 | Ruoslahti et al. | |
| 5,491,130 A | 2/1996 | Roberts et al. | |
| 5,510,328 A | 4/1996 | Polarek et al. ................ 38/16 |
| 5,780,436 A * | 7/1998 | Bhatnagar et al. | |

FOREIGN PATENT DOCUMENTS

WO    WO 96/39834    6/1996    ........... 43/40

WO    WO 97/41731    4/1997

OTHER PUBLICATIONS

Graham et al. 1993. Analysis of the Human T-Cell Response to Picornaviruses: Identification of T-Cell Epitopes Close to B-Cell Epitopes in Poliovirus. (Journal of Virology, Mar. vol. 67, No. 3, pp. 1627-1637).*
Donaldson et al., Journal of Cell Science, 1987 vol. 87, 525-534.*
Graham et al. 1993, Journal of Virology, vol. 67, No. 3, pp. 1627-1637.*
Jones et al. 1993, P.N.A.S. vol. 90, No. 22, pp. 10553-10557.*
Merriam-Webster's Online Dictionary, 10th Edition, 2003.*
Lobb et al (1991) Biochem, Biophys. Res. Comm. 178, 1498-1504.
Pantaloni et al (1996) J. Biol. Chem. 271, 22146-22151.
Shchelkunov et al (1993) FEBS Lett. 319, 80-83.
Graham et al (1993) J. Virol. 67, 1627-1637.
Chi et al (1994) Blood Coagulation, Fibrinolysis, Platelets, pp. 83-89.
Inoue et al (1997) Int Arch Allergy Immunol 114, 354-360.
Oberto et al (1989) J. Mol. Biol. 207, 675-693.
Aguado et al (1992) J. Gen. Virol. 73, 2887-2902.
Wang et al (1995) Proc Natl. Acad. Sci. USA 92, 5714-5718.
Schor et al (1996) J. Cell Science 109, 2581-2590.
Akiyama & Yamada (1985) J. Biol. Chem. 260(19), 10402-10405.
Humphries et al (1994) Exp. Opin, Ther. Patents 4, 227-235.
Schor, Ellis, Banyard & Schor (1999) J. Cell Science 112, 3879-3888.
Schor et al (1994) Prog. Growth Factor Res. 5, 223-248.
Schor et al (1993) In: Cell Behaviour: Adhesion and Motility (ed. G. Evans, C. Wigley and R. Warn) Society of Exp. Biol. Symp. 47, 235-251.
Grey et al (1989) Proc. Natl. Acad. Sci. USA 86, 2438-2442.
Cheng et al (1994) J. Med. Chem. 37, 1-8.
Saiki et al (1990) Jpn J. Cancer Res. 81, 668-675 (Abstract only).
Nicosia et al (1993) J. Cell. Physiol. 154, 654-661 (Abstract only).
Britsch et al (1989) Anat. Embryol. Berl. 180, 479-484 (Abstract only).
Nicosia & Bonanno (1991) Am. J. Pathol. 138, 829-833.
Greenspoon et al (1993) Biochemistry 32, 1001-1008.
The Extracellular Matrix Facts Book (ed Ayad et al), Academic Press, Ny, pp. 104-107.

* cited by examiner

*Primary Examiner*—Bruce R. Campell
*Assistant Examiner*—B. Dell Chism
(74) *Attorney, Agent, or Firm*—Knobbe, Martens, Olson & Bear LLP

(57) ABSTRACT

A compound with a relative molecular mass of less than 15000 comprising the peptide Ile-Gly-Asp (IGD) or a peptide or non-peptide mimic thereof. The compounds may be used to modulate cell migration and are useful in angiogenesis.

18 Claims, 7 Drawing Sheets

```
   1    MLRGPGPGLL   LLAVQCLGTA   VPSTGASKSK   RQAQQMVQPQ   SPVAVSQSKP
  51    GCYDNGKHYQ   INQQWERTYL   GNVLVCTCYG   GSRGFNCESK   PEAEETCFDK
 101    YTGNTYRVGD   TYERPKDSMI   WDCTCIGAGR   GRISCTIANR   CHEGGQSYKI
 151    GDTWRRPHET   GGYMLECVCL   GNGKGEWTCK   PIAEKCFDHA   AGTSYVVGET
 201    WEKPYQGWMM   VDCTCLGEGS   GRITCTSRNR   CNDQDTRTSY   RIGDTWSKKD
 251    NRGNLLQCIC   TGNRGEWKC    ERHTSVQTTS   SGSGPFTDVR   AAVYQPQPHP
 301    QPPPYGHCVT   DSGVVYSVGM   QWLKTQGNKQ   MLCTCLGNGV   SCQETAVTQT
 351    YGGNSNGEPC   VLPFTYNGRT   FYSCTTEGRQ   DGHLWCSTTS   NYEQDQKYSF
 401    CTDHTVLVQT   QGGNSNGALC   HFPFLYNNHN   YTDCTSEGRR   DNMKWCGTTQ
 451    NYDADQKFGF   CPMAAHEEIC   TTNEGVMYRI   GDQWDKQHDM   GHMMRCTCVG
 501    NGRGEWTCYA   YSQLRDQCIV   DDITYNVNDT   FHKRHEEGHM   LNCTCFGQGR
 551    GRWKCDPVDQ   CQDSETGTFY   QLGDSNEKYV   HGVRYQCYCY   GRGIGEWHCQ
 601    PLQTYPSSSG   PVEVFITETP   SQPNSHPIQW   NAPQPSHISK   YILRWRPKNS
 651    VGRWKEATIP   GHLNSYTIKG   LKPGVVYEGQ   LISIQQYGHQ   EVTRFDFTTT
 701    STSTPVTSNT   VTGETTPFSP   LVATSESVTE   ITASSFVVSW   VSASDTVSGF
 751    RVEYELSEEG   DEPQYLDLPS   TATSVNIPDL   LPGRKYIVNV   YQISEDGEQS
 801    LILSTSQTTA   PDAPPDPTVD   QVDDTSIVVR   WSRPQAPITG   YRIVYSPSVE
 851    GSSTELNLPE   TANSVTLSDL   QPGVQYNITI   YAVEENQEST   PVVIQQETTG
 901    TPRSDTVPSP   RDLQFVEVTD   VKVTIMWTPP   ESAVTGYRVD   VIPVNLPGEH
 951    GQRLPISRNT   FAEVTGLSPG   VTYYFKVFAV   SHGRESKPLT   AQQTTKLDAP
1001    TNLQFVNETD   STVLVRWTPP   RAQITGYRLT   VGLTRRGQPR   QYNVGPSVSK
1051    YPLRNLQPAS   EYTVSLVAIK   GNQESPKATG   VFTTLQPGSS   IPPYNTEVTE
1101    TTIVITWTPA   PRIGFKLGVR   PSQGGEAPRE   VTSDSGSIVV   SGLTPGVEYV
1151    YTIQVLRDGQ   ERDAPIVNKV   VTPLSPPTNL   HLEANPDTGV   LTVSWERSTT
1201    PDITGYRITT   TPTNGQQGNS   LEEVVHADQS   SCTFDNLSPG   LEYNVSVYTV
1251    KDDKESVPIS   DTIIPEVPQL   TDLSFVDITD   SSIGLRWTPL   NSSTIIGYRI
1301    TVVAAGEGIP   IFEDFVDSSV   GYYTVTGLEP   GIDYDISVIT   LINGGESAPT
1351    TLTQQTAVPP   PTDLRFTNIG   PDTMRVTWAP   PPSIDLTNFL   VRYSPVKNEE
1401    DVAELSISPS   DNAVVLTNLL   PGTEYVVSVS   SVYEQHESTP   LRGRQKTGLD
1451    SPTGIDFSDI   TANSFTVHWI   APRATITGYR   IRHHPEHFSG   RPREDRVPHS
1501    RNSITLTNLT   PGTEYVVSIV   ALNGREESPL   LIGQQSTVSD   VPRDLEVVAA
1551    TPTSLLISWD   APAVTVRYYR   ITYGETGGNS   PVQEFTVPGS   KSTATISGLK
1601    PGVDYTITVY   AVTGRGDSPA   SSKPISINYR   TEIDKPSQMQ   VTDVQDNSIS
1651    VKWLPSSSPV   TGYRVTTTPK   NGPGPTKTKT   AGPDQTEMTI   EGLQPTVEYV
1701    VSVYAQNPSG   ESQPLVQTAV   TNIDRPKGLA   FTDVDVDSIK   IAWESPQGQV
1751    SRYRVTYSSP   EDGIHELFPA   PDGEEDTAEL   QGLRPGSEYT   VSVVALHDDM
1801    ESQPLIGTQS   TAIPAPTDLK   FTQVTPTSLS   AQWTPPNVQL   TGYRVRVTPK
1851    EKTGPMKEIN   LAPDSSSVVV   SGLMVATKYE   VSVYALKDTL   TSRPAQGVVT
1901    TLENVSPPRR   ARVTDATETT   ITISWRTKTE   TITGFQVDAV   PANGQTPIQR
1951    TIKPDVRSYT   ITGLQPGTDY   KIYLYTLNDN   ARSSPVVIDA   STAIDAPSNL
2001    RFLATTPNSL   LVSWQPPRAR   ITGYIIKYEK   PGSPPREVVP   RPRPGVTEAT
2051    ITGLEPGTEY   TIYVIALKNN   QKSEPLIGRK   KTDELPQLVT   LPHPNLHGPE
2101    ILDVPSTVQK   TPFVTHPGYD   TGNGIQLPGT   SGQQPSVGQQ   MIFEEHGFRR
2151    TTPPTTATPI   RHRPRPYPPN   VGEEIQIGHI   PREDVDYHLY   PHGPGLNPNA
2201    STGQEALSQT   TISWAPFQDT   SEYIISCHPV   GTDEEPLQFR   VPGTSTSATL
2251    TGLTRGATYN   IIVEALKDQQ   RHKVREEVVT   VGNSVNEGLN   QPTDDSCFDP
2301    YTVSHYAVGD   EWERMSESGF   KLLCQCLGFG   SGHFRCDSSR   WCHDNGVNYK
2351    IGEKWDRQGE   NGQMMSCTCL   GNGKGEFKCD   PHEATCYDDG   KTYHVGEQWQ
2401    KEYLGAICSC   TCFGGQRGWR   CDNCRRPGGE   PSPEGTTGQS   YNQYSQRYHQ
2451    RTNTNVNCPI   ECFMPLDVQA   DREDSRE
```

*Fig. 5*

SEQUENCE LISTING

<160> NUMBER OF SEQ ID NOS: 13

<210> SEQ ID NO 1
<211> LENGTH: 3
<212> TYPE: PRT
<213> ORGANISM: Homo sapiens

<400> SEQUENCE: 1

-continued

```
Ile Gly Asp
1

<210> SEQ ID NO 2
<211> LENGTH: 4
<212> TYPE: PRT
<213> ORGANISM: Homo sapiens

<400> SEQUENCE: 2

Ile Gly Asp Ser
1

<210> SEQ ID NO 3
<211> LENGTH: 4
<212> TYPE: PRT
<213> ORGANISM: Homo sapiens

<400> SEQUENCE: 3

Ile Gly Asp Gln
1

<210> SEQ ID NO 4
<211> LENGTH: 3
<212> TYPE: PRT
<213> ORGANISM: Homo sapiens

<400> SEQUENCE: 4

Arg Gly Asp
1

<210> SEQ ID NO 5
<211> LENGTH: 4
<212> TYPE: PRT
<213> ORGANISM: Unknown
<220> FEATURE:
<223> OTHER INFORMATION: Conservative substitution for "D"

<400> SEQUENCE: 5

Ile Gly Glu Ser
1

<210> SEQ ID NO 6
<211> LENGTH: 4
<212> TYPE: PRT
<213> ORGANISM: Unknown
<220> FEATURE:
<223> OTHER INFORMATION: Peptide related to IGDS

<400> SEQUENCE: 6

Arg Gly Asp Ser
1

<210> SEQ ID NO 7
<211> LENGTH: 2477
<212> TYPE: PRT
<213> ORGANISM: Homo sapiens

<400> SEQUENCE: 7

Met Leu Arg Gly Pro Gly Pro Gly Leu Leu Leu Leu Ala Val Leu Cys
1               5                   10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45
```

```
Lys Pro Gly Cys Tyr Asp Asn Gly Lys His Tyr Gln Ile Asn Gln Gln
 50                  55                  60

Trp Glu Arg Thr Tyr Leu Gly Asn Val Leu Val Cys Thr Cys Tyr Gly
 65                  70                  75                  80

Gly Ser Arg Gly Phe Asn Cys Glu Ser Lys Pro Glu Ala Glu Glu Thr
                 85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
            260                 265                 270

His Thr Ser Val Gln Thr Thr Ser Ser Gly Ser Gly Pro Phe Thr Asp
        275                 280                 285

Val Arg Ala Ala Val Tyr Gln Pro Gln Pro His Pro Gln Pro Pro Pro
    290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
        355                 360                 365

Arg Thr Phe Tyr Ser Cys Thr Thr Glu Gly Arg Gln Asp Gly His Leu
    370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Gln Gly Gly Asn Ser Asn
                405                 410                 415

Gly Ala Leu Cys His Phe Pro Phe Leu Tyr Asn Asn His Asn Tyr Thr
            420                 425                 430

Asp Cys Thr Ser Glu Gly Arg Arg Asp Asn Met Lys Trp Cys Gly Thr
        435                 440                 445

Thr Gln Asn Tyr Asp Ala Asp Gln Lys Phe Gly Phe Cys Pro Met Ala
    450                 455                 460

Ala His Glu Glu Ile Cys Thr Thr Asn Glu Gly Val Met Tyr Arg Ile
```

-continued

```
            465                 470                 475                 480
Gly Asp Gln Trp Asp Lys Gln His Asp Met Gly His Met Met Arg Cys
                485                 490                 495
Thr Cys Val Gly Asn Gly Arg Gly Glu Trp Thr Cys Tyr Ala Tyr Ser
                500                 505                 510
Gln Leu Arg Asp Gln Cys Ile Val Asp Asp Ile Thr Tyr Asn Val Asn
                515                 520                 525
Asp Thr Phe His Lys Arg His Glu Glu Gly His Met Leu Asn Cys Thr
                530                 535                 540
Cys Phe Gly Gln Gly Arg Gly Arg Trp Lys Cys Asp Pro Val Asp Gln
545                 550                 555                 560
Cys Gln Asp Ser Glu Thr Gly Thr Phe Tyr Gln Ile Gly Asp Ser Trp
                565                 570                 575
Glu Lys Tyr Val His Gly Val Arg Tyr Gln Cys Tyr Cys Tyr Gly Arg
                580                 585                 590
Gly Ile Gly Glu Trp His Cys Gln Pro Leu Gln Thr Tyr Pro Ser Ser
                595                 600                 605
Ser Gly Pro Val Glu Val Phe Ile Thr Glu Thr Pro Ser Gln Pro Asn
                610                 615                 620
Ser His Pro Ile Gln Trp Asn Ala Pro Gln Pro Ser His Ile Ser Lys
625                 630                 635                 640
Tyr Ile Leu Arg Trp Arg Pro Lys Asn Ser Val Gly Arg Trp Lys Glu
                645                 650                 655
Ala Thr Ile Pro Gly His Leu Asn Ser Tyr Thr Ile Lys Gly Leu Lys
                660                 665                 670
Pro Gly Val Val Tyr Glu Gly Gln Leu Ile Ser Ile Gln Gln Tyr Gly
                675                 680                 685
His Gln Glu Val Thr Arg Phe Asp Phe Thr Thr Thr Ser Thr Ser Thr
                690                 695                 700
Pro Val Thr Ser Asn Thr Val Thr Gly Glu Thr Thr Pro Phe Ser Pro
705                 710                 715                 720
Leu Val Ala Thr Ser Glu Ser Val Thr Glu Ile Thr Ala Ser Ser Phe
                725                 730                 735
Val Val Ser Trp Val Ser Ala Ser Asp Thr Val Ser Gly Phe Arg Val
                740                 745                 750
Glu Tyr Glu Leu Ser Glu Glu Gly Asp Glu Pro Gln Tyr Leu Asp Leu
                755                 760                 765
Pro Ser Thr Ala Thr Ser Val Asn Ile Pro Asp Leu Leu Pro Gly Arg
                770                 775                 780
Lys Tyr Ile Val Asn Val Tyr Gln Ile Ser Glu Asp Gly Glu Gln Ser
785                 790                 795                 800
Leu Ile Leu Ser Thr Ser Gln Thr Thr Ala Pro Asp Ala Pro Pro Asp
                805                 810                 815
Pro Thr Val Asp Gln Val Asp Asp Thr Ser Ile Val Val Arg Trp Ser
                820                 825                 830
Arg Pro Gln Ala Pro Ile Thr Gly Tyr Arg Ile Val Tyr Ser Pro Ser
                835                 840                 845
Val Glu Gly Ser Ser Thr Glu Leu Asn Leu Pro Glu Thr Ala Asn Ser
                850                 855                 860
Val Thr Leu Ser Asp Leu Gln Pro Gly Val Gln Tyr Asn Ile Thr Ile
865                 870                 875                 880
Tyr Ala Val Glu Glu Asn Gln Glu Ser Thr Pro Val Val Ile Gln Gln
                885                 890                 895
```

```
Glu Thr Thr Gly Thr Pro Arg Ser Asp Thr Val Pro Ser Pro Arg Asp
            900                 905                 910

Leu Gln Phe Val Glu Val Thr Asp Val Lys Val Thr Ile Met Trp Thr
        915                 920                 925

Pro Pro Glu Ser Ala Val Thr Gly Tyr Arg Val Asp Val Ile Pro Val
        930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
            980                 985                 990

Gln Thr Thr Lys Leu Asp Ala Pro Thr Asn Leu Gln Phe Val Asn Glu
        995                 1000                1005

Thr Asp Ser Thr Val Leu Val Arg Trp Thr Pro Pro Arg Ala Gln
    1010                1015                1020

Ile Thr Gly Tyr Arg Leu Thr Val Gly Leu Thr Arg Arg Gly Gln
    1025                1030                1035

Pro Arg Gln Tyr Asn Val Gly Pro Ser Val Ser Lys Tyr Pro Leu
    1040                1045                1050

Arg Asn Leu Gln Pro Ala Ser Glu Tyr Thr Val Ser Leu Val Ala
    1055                1060                1065

Ile Lys Gly Asn Gln Glu Ser Pro Lys Ala Thr Gly Val Phe Thr
    1070                1075                1080

Thr Leu Gln Pro Gly Ser Ser Ile Pro Pro Tyr Asn Thr Glu Val
    1085                1090                1095

Thr Glu Thr Thr Ile Val Ile Thr Trp Thr Pro Ala Pro Arg Ile
    1100                1105                1110

Gly Phe Lys Leu Gly Val Arg Pro Ser Gln Gly Gly Glu Ala Pro
    1115                1120                1125

Arg Glu Val Thr Ser Asp Ser Gly Ser Ile Val Val Ser Gly Leu
    1130                1135                1140

Thr Pro Gly Val Glu Tyr Val Tyr Thr Ile Gln Val Leu Arg Asp
    1145                1150                1155

Gly Gln Glu Arg Asp Ala Pro Ile Val Asn Lys Val Val Thr Pro
    1160                1165                1170

Leu Ser Pro Pro Thr Asn Leu His Leu Glu Ala Asn Pro Asp Thr
    1175                1180                1185

Gly Val Leu Thr Val Ser Trp Glu Arg Ser Thr Thr Pro Asp Ile
    1190                1195                1200

Thr Gly Tyr Arg Ile Thr Thr Thr Pro Thr Asn Gly Gln Gln Gly
    1205                1210                1215

Asn Ser Leu Glu Glu Val Val His Ala Asp Gln Ser Ser Cys Thr
    1220                1225                1230

Phe Asp Asn Leu Ser Pro Gly Leu Glu Tyr Asn Val Ser Val Tyr
    1235                1240                1245

Thr Val Lys Asp Asp Lys Glu Ser Val Pro Ile Ser Asp Thr Ile
    1250                1255                1260

Ile Pro Glu Val Pro Gln Leu Thr Asp Leu Ser Phe Val Asp Ile
    1265                1270                1275

Thr Asp Ser Ser Ile Gly Leu Arg Trp Thr Pro Leu Asn Ser Ser
    1280                1285                1290
```

-continued

```
Thr Ile Ile Gly Tyr Arg Ile Thr Val Ala Ala Gly Glu Gly
    1295                1300            1305

Ile Pro Ile Phe Glu Asp Phe Val Asp Ser Ser Val Gly Tyr Tyr
    1310                1315            1320

Thr Val Thr Gly Leu Glu Pro Gly Ile Asp Tyr Asp Ile Ser Val
    1325                1330            1335

Ile Thr Leu Ile His Gly Gly Glu Ser Ala Pro Thr Thr Leu Thr
    1340                1345            1350

Gln Gln Thr Ala Val Pro Pro Thr Asp Leu Arg Phe Thr Asn
    1355                1360            1365

Ile Gly Pro Asp Thr Met Arg Val Thr Trp Ala Pro Pro Ser
    1370                1375            1380

Ile Asp Leu Thr Asn Phe Leu Val Arg Tyr Ser Pro Val Lys Asn
    1385                1390            1395

Glu Glu Asp Val Ala Glu Leu Ser Ile Ser Pro Ser Asp Asn Ala
    1400                1405            1410

Val Val Leu Thr Asn Leu Leu Pro Gly Thr Glu Tyr Val Val Ser
    1415                1420            1425

Val Ser Ser Val Tyr Glu Gln His Glu Ser Thr Pro Leu Arg Gly
    1430                1435            1440

Arg Gln Lys Thr Gly Leu Asp Ser Pro Thr Gly Ile Asp Phe Ser
    1445                1450            1455

Asp Ile Thr Ala Asn Ser Phe Thr Val His Trp Ile Ala Pro Arg
    1460                1465            1470

Ala Thr Ala Thr Gly Tyr Arg Ile Arg His His Pro Glu His Phe
    1475                1480            1485

Ser Gly Arg Pro Arg Glu Asp Arg Val Pro His Ser Arg Asn Ser
    1490                1495            1500

Ile Thr Leu Thr Asn Leu Thr Pro Gly Thr Glu Tyr Val Val Ser
    1505                1510            1515

Ile Val Ala Leu Asn Gly Arg Glu Glu Ser Pro Leu Leu Ile Gly
    1520                1525            1530

Gln Gln Ser Thr Val Ser Asp Val Pro Arg Asp Leu Glu Val Val
    1535                1540            1545

Ala Ala Thr Pro Thr Ser Leu Leu Ile Ser Trp Asp Ala Pro Ala
    1550                1555            1560

Val Thr Val Arg Tyr Tyr Arg Ile Thr Tyr Gly Glu Thr Gly Gly
    1565                1570            1575

Asn Ser Pro Val Gln Glu Phe Thr Val Pro Gly Ser Lys Ser Thr
    1580                1585            1590

Ala Thr Ile Ser Gly Leu Lys Pro Gly Val Asp Tyr Thr Ile Thr
    1595                1600            1605

Val Tyr Ala Val Thr Gly Arg Gly Asp Ser Pro Ala Ser Ser Lys
    1610                1615            1620

Pro Ile Ser Ile Asn Tyr Arg Thr Glu Ile Asp Lys Pro Ser Gln
    1625                1630            1635

Met Gln Val Thr Asp Val Gln Asp Asn Ser Ile Ser Val Arg Trp
    1640                1645            1650

Leu Pro Ser Ser Ser Pro Val Thr Gly Tyr Arg Val Thr Thr Thr
    1655                1660            1665

Pro Lys Asn Gly Pro Gly Pro Thr Lys Thr Lys Thr Ala Gly Pro
    1670                1675            1680

Asp Gln Thr Glu Met Thr Ile Glu Gly Leu Gln Pro Thr Val Glu
```

-continued

```
            1685                1690                1695

Tyr Val Val Ser Val Tyr Ala Gln Asn Pro Ser Gly Glu Ser Gln
        1700                1705                1710

Pro Leu Val Gln Thr Ala Val Thr Asn Ile Asp Arg Pro Lys Gly
        1715                1720                1725

Leu Ala Phe Thr Asp Val Asp Val Asp Ser Ile Lys Ile Ala Trp
        1730                1735                1740

Glu Ser Pro Gln Gly Gln Val Ser Arg Tyr Arg Val Thr Tyr Ser
        1745                1750                1755

Ser Pro Glu Asp Gly Ile His Glu Leu Phe Pro Ala Pro Asp Gly
        1760                1765                1770

Glu Glu Asp Thr Ala Glu Leu Gln Gly Leu Arg Pro Gly Ser Glu
        1775                1780                1785

Tyr Thr Val Ser Val Val Ala Leu His Asp Asp Met Glu Ser Gln
        1790                1795                1800

Pro Leu Ile Gly Thr Gln Ser Thr Ala Ile Pro Ala Pro Thr Asp
        1805                1810                1815

Leu Lys Phe Thr Gln Val Thr Pro Thr Ser Leu Ser Ala Gln Trp
        1820                1825                1830

Thr Pro Pro Asn Val Gln Leu Thr Gly Tyr Arg Val Arg Val Thr
        1835                1840                1845

Pro Lys Glu Lys Thr Gly Pro Met Lys Glu Ile Asn Leu Ala Pro
        1850                1855                1860

Asp Ser Ser Ser Val Val Val Ser Gly Leu Met Val Ala Thr Lys
        1865                1870                1875

Tyr Glu Val Ser Val Tyr Ala Leu Lys Asp Thr Leu Thr Ser Arg
        1880                1885                1890

Pro Ala Gln Gly Val Val Thr Thr Leu Glu Asn Val Ser Pro Pro
        1895                1900                1905

Arg Arg Ala Arg Val Thr Asp Ala Thr Glu Thr Thr Ile Thr Ile
        1910                1915                1920

Ser Trp Arg Thr Lys Thr Glu Thr Ile Thr Gly Phe Gln Val Asp
        1925                1930                1935

Ala Val Pro Ala Asn Gly Gln Thr Pro Ile Gln Arg Thr Ile Lys
        1940                1945                1950

Pro Asp Val Arg Ser Tyr Thr Ile Thr Gly Leu Gln Pro Gly Thr
        1955                1960                1965

Asp Tyr Lys Ile Tyr Leu Tyr Thr Leu Asn Asp Asn Ala Arg Ser
        1970                1975                1980

Ser Pro Val Val Ile Asp Ala Ser Thr Ala Ile Asp Ala Pro Ser
        1985                1990                1995

Asn Leu Arg Phe Leu Ala Thr Thr Pro Asn Ser Leu Leu Val Ser
        2000                2005                2010

Trp Gln Pro Pro Arg Ala Arg Ile Thr Gly Tyr Ile Ile Lys Tyr
        2015                2020                2025

Glu Lys Pro Gly Ser Pro Pro Arg Glu Val Val Pro Arg Pro Arg
        2030                2035                2040

Pro Gly Val Thr Glu Ala Thr Ile Thr Gly Leu Glu Pro Gly Thr
        2045                2050                2055

Glu Tyr Thr Ile Tyr Val Ile Ala Leu Lys Asn Asn Gln Lys Ser
        2060                2065                2070

Glu Pro Leu Ile Gly Arg Lys Lys Thr Asp Glu Leu Pro Gln Leu
        2075                2080                2085
```

-continued

```
Val Thr Leu Pro His Pro Asn Leu His Gly Pro Glu Ile Leu Asp
    2090            2095            2100

Val Pro Ser Thr Val Gln Lys Thr Pro Phe Val Thr His Pro Gly
    2105            2110            2115

Tyr Asp Thr Gly Asn Gly Ile Gln Leu Pro Gly Thr Ser Gly Gln
    2120            2125            2130

Gln Pro Ser Val Gly Gln Gln Met Ile Phe Glu Glu His Gly Phe
    2135            2140            2145

Arg Arg Thr Thr Pro Pro Thr Thr Ala Thr Pro Ile Arg His Arg
    2150            2155            2160

Pro Arg Pro Tyr Pro Pro Asn Val Gly Glu Glu Ile Gln Ile Gly
    2165            2170            2175

His Ile Pro Arg Glu Asp Val Asp Tyr His Leu Tyr Pro His Gly
    2180            2185            2190

Pro Gly Leu Asn Pro Asn Ala Ser Thr Gly Gln Glu Ala Leu Ser
    2195            2200            2205

Gln Thr Thr Ile Ser Trp Ala Pro Phe Gln Asp Thr Ser Glu Tyr
    2210            2215            2220

Ile Ile Ser Cys His Pro Val Gly Thr Asp Glu Glu Pro Leu Gln
    2225            2230            2235

Phe Arg Val Pro Gly Thr Ser Thr Ser Ala Thr Leu Thr Gly Leu
    2240            2245            2250

Thr Arg Gly Ala Thr Tyr Asn Ile Ile Val Glu Ala Leu Lys Asp
    2255            2260            2265

Gln Gln Arg His Lys Val Arg Glu Val Val Thr Val Gly Asn
    2270            2275            2280

Ser Val Asn Glu Gly Leu Asn Gln Pro Thr Asp Asp Ser Cys Phe
    2285            2290            2295

Asp Pro Tyr Thr Val Ser His Tyr Ala Val Gly Asp Glu Trp Glu
    2300            2305            2310

Arg Met Ser Glu Ser Gly Phe Lys Leu Leu Cys Gln Cys Leu Gly
    2315            2320            2325

Phe Gly Ser Gly His Phe Arg Cys Asp Ser Ser Arg Trp Cys His
    2330            2335            2340

Asp Asn Gly Val Asn Tyr Lys Ile Gly Glu Lys Trp Asp Arg Gln
    2345            2350            2355

Gly Glu Asn Gly Gln Met Met Ser Cys Thr Cys Leu Gly Asn Gly
    2360            2365            2370

Lys Gly Glu Phe Lys Cys Asp Pro His Glu Ala Thr Cys Tyr Asp
    2375            2380            2385

Asp Gly Lys Thr Tyr His Val Gly Glu Gln Trp Gln Lys Glu Tyr
    2390            2395            2400

Leu Gly Ala Ile Cys Ser Cys Thr Cys Phe Gly Gly Gln Arg Gly
    2405            2410            2415

Trp Arg Cys Asp Asn Cys Arg Arg Pro Gly Gly Glu Pro Ser Pro
    2420            2425            2430

Glu Gly Thr Thr Gly Gln Ser Tyr Asn Gln Tyr Ser Gln Arg Tyr
    2435            2440            2445

His Gln Arg Thr Asn Thr Asn Val Asn Cys Pro Ile Glu Cys Phe
    2450            2455            2460

Met Pro Leu Asp Val Gln Ala Asp Arg Glu Asp Ser Arg Glu
    2465            2470            2475
```

```
<210> SEQ ID NO 8
<211> LENGTH: 5
<212> TYPE: PRT
<213> ORGANISM: Homo sapiens

<400> SEQUENCE: 8

Ile Asp Ala Pro Ser
1               5

<210> SEQ ID NO 9
<211> LENGTH: 3
<212> TYPE: PRT
<213> ORGANISM: Homo sapiens

<400> SEQUENCE: 9

Leu Asp Val
1

<210> SEQ ID NO 10
<211> LENGTH: 4
<212> TYPE: PRT
<213> ORGANISM: Homo sapiens

<400> SEQUENCE: 10

Arg Glu Asp Val
1

<210> SEQ ID NO 11
<211> LENGTH: 4
<212> TYPE: PRT
<213> ORGANISM: Unknown
<220> FEATURE:
<223> OTHER INFORMATION: Peptide related to IGES

<400> SEQUENCE: 11

Arg Gly Glu Ser
1

<210> SEQ ID NO 12
<211> LENGTH: 5
<212> TYPE: PRT
<213> ORGANISM: Homo sapiens

<400> SEQUENCE: 12

Pro His Ser Arg Asn
1               5

<210> SEQ ID NO 13
<211> LENGTH: 4
<212> TYPE: PRT
<213> ORGANISM: Homo sapiens

<400> SEQUENCE: 13

Arg Gly Asp Asp
1
```

PEPTIDES CONTAINING THE MOTIF IGD AND THEIR USE AS CELL MIGRATION MODULATORS

BACKGROUND OF THE INVENTION

1. Field of the Invention

The present invention relates to peptides and related compounds and in particular to peptides and related compounds which affect cell migration.

2. Description of the Related Art

Fibronectin is a widely distributed glycoprotein present at high concentrations in most extracellular matrices, in plasma (300 µg/ml), and in other body fluids. Fibronectin is a prominent adhesive protein and mediates various aspects of cellular interactions with extracellular matrices including migration. Its principal functions appear to be in cellular migration during development and wound healing, regulation of cell growth and differentiation, and haemostasis/thrombosis.

Fibronectin is a dimer of two non-identical subunits covalently linked near their COOH-termini by a pair of disulphide bonds. The difference between the subunits is determined by alternative splicing of the IIICS (or V) region. In the insoluble, matrix form of fibronectin, the dimer associates into disulphide-bonded oligomers and fibrils, while soluble, body fluid fibronectin is predominantly dimeric. Three regions of fibronectin are subject to alternative splicing and in general the matrix form of the molecule has a higher content of these segments than the soluble form. The human IIICS region has five potential variations, while the rat, bovine and chicken sequences have three, three and two, respectively. Each subunit is composed of a series of structurally independent domains linked by flexible polypeptide segments. At the primary sequence level, the origin of the majority of the fibronectin molecule can be accounted for by endoduplication of three types of polypeptide repeat. Different fibronectin domains are specialized for binding extracellular matrix macromolecules or bacterial or eukaryotic membrane receptors. The central cell-binding domain is recognised by most adherent cells via the integrin receptors α3β1, α5β1, αVβ1, αIIbβ3, αVβ3, αVβ5 and αVβ6. The IIICS/HepII cell-binding domain is recognised by lymphoid cells, neural crest derivatives and myoblasts via the integrins α4β1 and α4β7. Several peptide active sites have been identified in these domains.

Plasma fibronectin can be purified by a combination of gelatin and heparin affinity chromatography. Cell-associated fibronectin can be extracted from culture monolayers with 1 M urea. Further details on fibronectin are in *The Extracellular Matrix Facts Book*, Ayad et al (eds), Academic Press, Harcourt Brace & Company, London.

Limited proteolytic digestion of fibronectin results in the release of a number of its functional domains, which are characterised by their specific adhesion to other matrix macromolecules or integrin receptors on the cell surface (i.e. the cell-binding domain)[1]. The transmembrane assay has commonly been used to study the effects of fibronectin and its purified functional domains on cell migration in vitro. Essentially, this assay involves assessing cell movement through a polycarbonate membrane coated with an adhesive protein (usually gelatin) separating upper and lower medium compartments containing the putative effector molecule. Previous studies have revealed that nano- to micromolar concentrations of fibronectin and its purified cell-binding domain stimulate the migration of a wide range of cell types in the transmembrane assay[2,3]. Related studies implicated the RGD (SEQ ID NO 4) amino acid motif (located in the tenth type III repeat module) in mediating these effects of both native fibronectin and its cell-binding domain[3]. Significantly, small RGD-containing synthetic peptides did not stimulate cell migration; indeed, these peptides inhibited the adhesive and migration stimulating activity of larger protein domains containing the RGD (SEQ ID NO 4) motif by competition for receptor ligation[4]. In contrast to the activity of the cell-binding domain, the gelatin-binding domain of fibronectin has consistently been reported to be devoid of migration stimulating activity in the transmembrane assay[2,5].

Schor et al (1994) *Progress in Growth Factor Research* 5, 223–248 is a review of cytokine control of cell motility and its modulation and mediation by the extracellular matrix. Schor et al (1993) In: *Cell Behaviour: Adhesion and Motility* (ed. G. Evans, C. Wigley and R. Warn) Society of Experimental Biology Symposium No. 47, pages 235–251 relates to migration stimulating factor (MSF).

Grey et al (1989) *Proc. Natl. Acad. Sci. USA* 86, 2438–2442 relates to the purification of the MSF produced by fetal and breast cancer patient fibroblasts.

U.S. Pat. No. 5,300,630 relates to oncodevelopmentally regulated antigens related to fibronectin.

U.S. Pat. No. 5,510,328 relates to methods of reducing or inhibiting wound contraction using certain peptides.

U.S. Pat. No. 5,354,736 relates to compounds that have enhanced cell binding with respect to collagen.

U.S. Pat. No. 4,976,734 relates to a method of stimulating chemotaxis towards a prosthetic device.

U.S. Pat. No. 4,980,279 relates to portions of fibronectin.

U.S. Pat. No. 5,049,658 relates to a polypeptide having the cell-spreading activity of human fibronectin.

U.S. Pat. No. 5,124,155 relates to wound healing dressings, which are prepared by flocculating fibronectin.

U.S. Pat. No. 5,453,489 relates to polypeptides, which encompass fibronectin—fibronectin binding sites and which are capable of inhibiting fibronectin matrix assembly.

U.S. Pat. No. 5,192,746 relates to compounds having the property of modulating cell adhesion.

U.S. Pat. No. 5,491,130 relates to peptides derived from human endothelial cell thrombosponding, which bind to the gelatin-binding domain of fibronectin.

SUMMARY OF THE INVENTION

We have previously developed an alternative migration assay involving the assessment of cell movement into gels of native type I collagen fibres[6]. Using this assay, we have recently reported that femtomolar concentrations of the gelatin-binding domain stimulated the migration of human dermal fibroblasts, whilst native fibronectin and its cell-binding domain were inactive[7].

We observed that the gelatin-binding domain did indeed stimulate cell migration in the transmembrane assay when filters were coated with native collagen, but not with gelatin (as used in the majority of previous studies). One of the objectives of the present study has been to determine whether a candidate amino acid sequence within the gelatin-binding domain of fibronectin is responsible for its substratum-dependent stimulation of cell migration and, if so, the manner in which it may be functionally related to the RGD (SEQ ID NO 4) motif. Surprisingly we have found that peptides and other molecules containing the IGD (SEQ ID NO 1) amino acid sequence motif stimulate fibroblast migration into native but not denatured collagen substrate.

A first aspect of the invention provides a compound with a relative molecular 20 mass of less than 15 000 comprising the peptide Ile-Gly-Asp (IGD) (SEQ ID NO 1) or a peptide or non-peptide mimic thereof.

Preferably, the compound has a relative molecular mass of less than 12000, more preferably less than 10000.

We have found that, surprisingly, the peptide IGD (SEQ ID NO 1) alone or when present as a moiety in a larger molecule is able to modulate cell migration. Thus, the preferred compounds of the invention are those, which are able to modulate cell migration under appropriate conditions such as those conditions described in the Examples.

By peptide mimic of IGD (SEQ ID NO 1) we include that the Ile is replaced by another hydrophobic amino acid such as Val, Leu, Phe, Trp or Tyr, most preferably Val or Leu. We also include that the Asp is replaced by Glu. Less preferably the Gly residue is replaced by Ala. The peptide mimics are preferably those that exhibit substantially the same cell migration modulating activity of a peptide comprising the peptide sequence IGD (SEQ ID NO 1) and, more preferably substantially the same cell migration modulating activity of any one of the peptides IGD (SEQ ID NO 1) or IGDS (SEQ ID NO 2) or IGDQ (SEQ ID NO 3). Suitably, the peptide mimic comprises a moiety, which has substantially the same charge distribution and/or spatial configuration as any one of the peptides IGD (SEQ ID NO 1) or IGDS (SEQ ID NO 2) or IGDQ (SEQ ID NO 3).

By non-peptide mimics of IGD (SEQ ID NO 1) we include a moiety which has the same charge distribution and/or spatial configuration as any one of the peptides IGD (SEQ ID NO 1) or IGDS (SEQ ID NO 2) or IGDQ (SEQ ID NO 3), and we include a moiety which has substantially the same cell migration modulating activity of a peptide comprising the IGD (SEQ ID NO 1) sequence.

Non-peptide surrogates of the RGD (SEQ ID NO 4) sequence have been developed or are described by, for example, Greenspoon et al (1993) *Biochemistry* 32, 1001–1008 and Humphries et al (1994) *Exp. Opin. Ther.* U.S. Pat. No. 4, 227–235, both of which are incorporated herein by reference, and suitable non-peptide mimics based on the IGD (SEQ ID NO 1) motif can be made using similar principles as for the non-peptide mimics of RGD. It can be well appreciated that I can be substituted for R and that the resulting peptides can be tested for cell increasing migration activity using the techniques described herein.

In Greenspoon et al., the design and preparation of nonpeptide analogues of RGD are described as follows. Compounds SF-6,5 and SFN-70 were prepared by coupling of methyl-5-aminovaleric acid with N-(butyloxycarbonyl)-6-aminohexanoic acid. The reaction was carried out using the 1,3-dicyclohexylcarbodiimide and 1 hydroxybenzotriazole in tetrahydroduran procedure. The butyloxycarbonyl protecting group was then removed by 50% trifluoroacetic acid in dichloromethane. Removal of the methyl ester protecting group was carried out with sodium hydroxide at pH 9.5, yielding SFN-70. The amine was converted to guanidium using 3,5-dimethylpyrazole-1-carboxamidine nitrate at pH 9.5 t produce the compound designated SF-6,5. Compound SF-6,6 was prepared from methyl-6-aminohexanoic acid and N-(butyloxycarbonyl)-6-aminohexanoic acid under the same conditions as used for SF-6,5. GK-5,5 was prepared from methyl-5-aminovaleric acid and N-(butyloxycarbonyl)-5-aminovaleric acid. Compounds AC-4 and AC-14 were prepared by stepwise synthesis either in solution or on a Merrifield resin, followed by deprotection and conversion of the amine to the guanidinium by the above-described methods. The final compounds were purified on preparative RP-18 columns and were judged pure by thin-layer chromatography (single spot) and $^1$H NMR spectroscopy. Compounds were characterized by $^1$H NMR and FAB-MS spectroscopy. The structures deduced from spectroscopy were consistent with the assigned structure. (Table 1). Table 1 shows a schematic presentation of the RGD-NH$_2$ peptide and the corresponding non-peptide surrogates. Note that the distance between positions a and b is 11 atoms.

TABLE 1

| Compound | | No. of atoms in the spacer |
|---|---|---|
| RGD-NH$_2$ | | |
| SF-6,5 | | 11 |
| AC-4 | | 11 |

TABLE 1-continued

| Compound | Structure | No. of atoms in the spacer |
|---|---|---|
| | RGD-NH₂ | |
| AC-14 | | 11 |
| SF-6,6 | | 12 |
| SFN-70 | | 11 |
| GK-5,5 | | 10 |

In Humphries et al., the design of nonpeptide analogues of RGD are described as follows. Complete deletion of the acidic functionality is tolerated in special circumstances, as with the antiparasitic drug, pentamidine, which possesses two amidinium groups and can perturb αIIbβ3 function. Simple des-aspartyl basic motifs have also been selected in peptide library panning studies with αIIbβ3. The backbone scaffold to which these key functions are attached can be simplified and varied in remarkable fashion. The more potent antagonists tend to replicate the hydrophilic character of the native peptide backbone to some degree, although there is no obvious requirement for hydrogen bonding to the receptor. Indeed, simple flexible constructs or constrained hydrocarbon scaffolds still possess marked affinity. Table 2 shows a survey of synthetic RGD analogues.

TABLE 2

| Compound | Source | Reference |
|---|---|---|
| | Smith Kline & French | J. Am. Chem. Soc. (1992) 114: 9615–9623 |
| | Merck | J. Med. Chem. (1992) 35, 4640–4642 |

TABLE 2-continued

| Compound | Source | Reference |
|---|---|---|
|  | Glaxo | Glaxo, EP-542363-A |
|  | Hoffman-La Roche | Hoffman-La Roche, EP-372486-A2 |
| 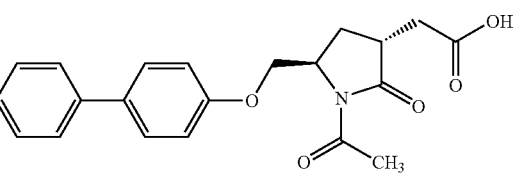 | Dr. Karl Thomae | Dr. Karl Thomae, EP-483667-A2 |
| 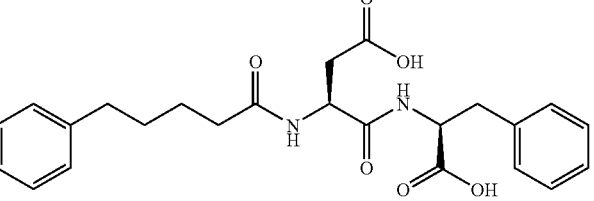 | GD Searle | GD Searle, EP-502536-A1 |
| 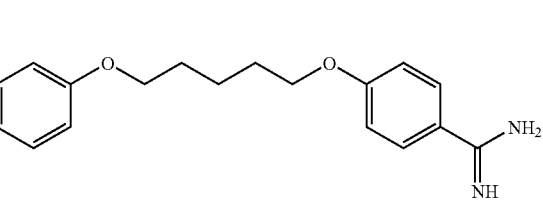 | [Pentamidine] | Thromb. Haemostasis (1992) 68(6):731–736 |
| 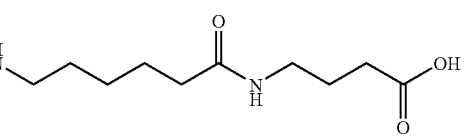 | Greenspoon et al. | Biochemistry (1993) 32:1001–1008 |
| 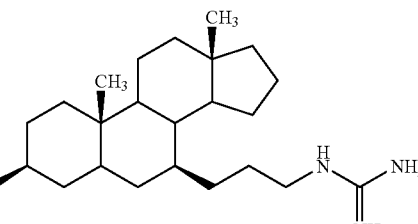 | Hirschmann et al. | Tetrahedron (1993) 49(17):3665–3676 |

Compounds which exhibit substantially the same cell migration modulating activity of a peptide comprising the peptide Ile-Gly-Asp (IGD) (SEQ ID NO 1) can be selected using a suitable screening system. The preferred screening system uses a migration assay similar to that described in Example 1 in which cell migration is assessed on a native type I collagen substratum (for example, collagen gel or transmembrane assay using collagen-coated membranes). Mimics are compounds which exhibit substantially the same effect as the peptides IGD (SEQ ID NO 1) or IGDS (SEQ ID NO 2) or IGDQ (SEQ ID NO 3) and which may act in an additive fashion with them. Inhibitors would abrogate the bioactivity of the peptides IGD (SEQ ID NO 1) or IGDS (SEQ ID NO 2) or IGDQ (SEQ ID NO 3). The peptide IGD (SEQ ID NO 1) and the gel-binding domain (GBD) act in an additive fashion, whereas the RGD (SEQ ID NO 4) peptide is an inhibitor of the IGD (SEQ ID NO 1) peptide.

Although the peptide sequence IGD (SEQ ID NO 1), when present in a compound of the invention, is sufficient to modulate cell migration it is preferred if the peptide sequence Ile-Gly-Asp-Ser (IGDS) or Ile-Gly-Asp-Gln (IGDQ)(SEQ ID NO 3) is present in a compound of the invention.

We have found, in relation to the peptides IGDS (SEQ ID NO 2), and IGD (SEQ ID NO 1) that is more potent than IGDQ (SEQ ID NO 3) which is more potent than IGD (SEQ ID NO 1) in stimulating fibroblast migration and so it is preferred if the compound comprises the peptide IGDS (SEQ ID NO 2).

It is preferred that the amino acids within the peptide sequence IGD (SEQ ID NO 1) or IGDS (SEQ ID NO 2) or IGDQ (SEQ ID NO 3), when present in the compounds of the invention, are all in the L configuration as is the case for natural amino acids. It will, nevertheless, be appreciated that when the compound of the invention is a peptide comprising IGD (SEQ ID NO 1) or IGDS (SEQ ID NO 2) or then the other amino acids within the peptide (ie those other than the ones in the IGD (SEQ ID NO 1) or IGDS (SEQ ID NO 2) or IGDQ (SEQ ID NO 3) moiety may be in the L- or D-configurations. In as much as peptides containing D-amino acids may be more resistant to proteolysis compounds containing D-amino acids (other than in the IGD (SEQ ID NO 1) or IGDS (SEQ ID NO 2) or IGDQ (SEQ ID NO 3) moiety may be preferred.

The invention covers all compounds with a relative molecular mass of less than 15 000 comprising the peptide IGD (SEQ ID NO 1) or a peptide or non-peptide mimic thereof; however, it is particularly preferred if the compound is a peptide comprising the peptide moiety IGD (SEQ ID NO 1). In other words, preferred compounds are peptides larger than 3 amino acids which contain the peptide moiety IGD (SEQ ID NO 1). Such peptides include the peptides IGDS (SEQ ID NO 2) and IGDQ (SEQ ID NO 3) and also include peptides with additional amino acids N terminal and/or C terminal to these motifs.

The compounds of the invention also include peptides wherein the IGD (SEQ ID NO 1) or IGDS (SEQ ID NO 2) or IGDQ (SEQ ID NO 3) moiety is masked by, for example, blocking groups being present on free —NH2 or —COOH groups. Preferably, such blocking groups are ones which may be removed readily in vivo, for example by hydrolysis; however, in some circumstances it may be desirable if the blocking groups are substantially resistant to hydrolysis.

The peptide IGD (SEQ ID NO 1) is also a compound of the invention.

It is preferred if the compounds have a relative molecular mass of less than 8000, preferably less than 6000, more preferably less than 5000, and preferably less than 2000. When the compound of the invention is a peptide it is preferred if the peptide has between 4 and 80 amino acid residues, more preferably between 4 and 50, still more preferably between 4 and 30 and preferably between 4 and 20 amino acid residues.

The compound of the invention may have a linear configuration or it may be branched or circular. When the compound of the invention is a peptide it may be linear, branched or circular.

It will be appreciated that the compound of the invention may comprise more than one IGD (SEQ ID NO 1) peptide moiety or a peptide or non-peptide mimic thereof. In certain circumstances it is advantageous for the compound of the invention to comprise between two and 50 such peptide moieties or a peptide or non-peptide mimics thereof, more preferably between 2 and 20 and most preferably between 5 and 15 such peptide moieties or peptide or non-peptide mimics thereof.

Thus, the peptide of the invention may consist of multiple repeats of IGD (SEQ ID NO 1) or IGDS (SEQ ID NO 2) or IGDQ (SEQ ID NO 3) or a peptide sequence containing conservative substitutions for I, G or D (such as IGES (SEQ ID NO 5)), and it may consist of any of these, including multiple repeats, in a cyclic form.

When the compound of the invention is a peptide it is possible for it to contain tandem repeats of the IGD-containing moiety (such as IGD (SEQ ID NO 1) itself or IGDS (SEQ ID NO 2) or IGDQ (SEQ ID NO 3) or combinations thereof).

Although not essential, it is preferred if the peptide of the invention comprises the IGD (SEQ ID NO 1) motif and flanking regions from the fibronectin molecule. For example, the flanking regions may be 1, 2, 3, 4, 5 or more amino acid residues on one or both sides of the occurrence of IGD (SEQ ID NO 1) in the fibronectin molecule. The amino acid sequence of the human fibronectin molecule is given in FIG. 5. Peptides containing flanking regions of fibronectin may have greater bioactivity than shorter tri- and tetrapeptides. These flanking regions are preferably derived from the seventh (for IGDQ (SEQ ID NO 3)) and ninth (for IGDS (SEQ ID NO 2)) type I repeat modules for fibronectin. It is also preferred if the compounds of the invention are the intact fibronectin type I repeat modules (17 and 19) since these may exhibit higher bioactivity than shorter synthetic peptides. Each of these type I modules contains approximately 45 amino acids and, preferably up to three of these modules are used in tandem array.

When the compound of the invention is a peptide it may be synthesised using well-known methods in the art. For example, peptides may be synthesised by the Fmoc-polyamide mode of solid-phase peptide synthesis as disclosed by Lu et al (1981) *J. Org. Chem.* 46, 3433 and references therein. Temporary N-amino group protection is afforded by the 9-fluorenylmethyloxycarbonyl (Fmoc) group. Repetitive cleavage of this highly base-labile protecting group is effected using 20% piperidine in N,N-dimethylformamide. Sidechain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalising agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N,N-dicyclohexyl-carbodiimide/1-hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of sidechain protecting groups by treatment with 95% trifluoroacetic acid containing a 50% scavenger mix. Scavengers commonly used are ethanedithiol, phenol, anisole and water, the exact choice depending on the constituent amino acids of the peptide being synthesised. Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from Calbiochem-Novabiochem (UK) Ltd, Nottingham NG7 2QJ, UK. Purification may be effected by any one, or a combination of, techniques such as size exclusion chromatography, ion-exchange chromatography and (principally) reverse-phase high performance liquid chromatography. Analysis of peptides may be carried out using thin layer chromatography, reverse-phase high performance liquid chromatography, amino-acid analysis after acid hydrolysis and by fast atom bombardment (FAB) mass spectrometric analysis.

Alternatively, when the peptide of the invention is of a suitable size, such as greater than about 50 residues in length, it may be desirable to produce the peptide by recombinant DNA technology.

The peptides of the invention may be encoded by a suitable polynucleotide which may be obtained or synthesised by methods well known in the art.

The DNA is then expressed in a suitable host to produce a peptide comprising the compound of the invention. Thus, the DNA encoding the peptide constituting the compound of the invention may be used in accordance with known techniques, appropriately modified in view of the teachings contained herein, to construct an expression vector, which is then used to transform an appropriate host cell for the expression and production of the peptide of the invention. Such techniques include those disclosed in U.S. Pat. No. 4,440,859 issued 3 Apr. 1984 to Rutter et al, U.S. Pat. No. 4,530,901 issued 23 Jul. 1985 to Weissman, U.S. Pat. No. 4,582,800 issued 15 Apr. 1986 to Crowl, U.S. Pat. No. 4,677,063 issued 30 Jun. 1987 to Mark et al, U.S. Pat. No. 4,678,751 issued 7 Jul. 1987 to Goeddel, U.S. Pat. No. 4,704,362 issued 3 Nov. 1987 to Itakura et al, U.S. Pat. No. 4,710,463 issued 1 Dec. 1987 to Murray, U.S. Pat. No. 4,757,006 issued 12 Jul. 1988 to Toole, Jr. et al, U.S. Pat. No. 4,766,075 issued 23 Aug. 1988 to Goeddel et al and U.S. Pat. No. 4,810,648 issued 7 Mar. 1989 to Stalker, all of which are incorporated herein by reference.

The DNA encoding the peptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the peptide, which can then be recovered.

Many expression systems are known, including bacteria (for example *E. coli* and *Bacillus subtilis*), yeasts (for example *Saccharomyces cerevisiae*), filamentous fungi (for example *Aspergillus*), plant cells, animal cells and insect cells.

The vectors include a prokaryotic replicon, such as the ColE1 ori, for propagation in a prokaryote, even if the vector is to be used for expression in other, non-prokaryotic, cell types. The vectors can also include an appropriate promoter such as a prokaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical prokaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA.

A typical mammalian cell vector plasmid is pSVL available from Pharmacia, Piscataway, N.J., USA. This vector uses the SV40 late promoter to drive expression of cloned genes, the highest level of expression being found in T antigen-producing cells, such as COS-1 cells.

An example of an inducible mammalian expression vector is pMSG, also available from Pharmacia. This vector uses the glucocorticoid-inducible promoter of the mouse mammary tumour virus long terminal repeat to drive expression of the cloned gene.

Useful yeast plasmid vectors are pRS403–406 and pRS413–416 and are generally available from Stratagene Cloning Systems, La Jolla, Calif. 92037, USA. Plasmids pRS403, pRS404, pRS405 and pRS406 are Yeast Integrating plasmids (Yips) and incorporate the yeast selectable markers HIS3, TRP1, LEU2 and URA3. Plasmids pRS413–416 are Yeast Centromere plasmids (YCps).

A variety of methods have been developed to operably link DNA to vectors via complementary cohesive termini. For instance, complementary homopolymer tracts can be added to the DNA segment to be inserted to the vector DNA. The vector and DNA segment are then joined by hydrogen bonding between the 5 complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or *E. coli* DNA polymerase I, enzymes that remove protruding, 3'-single-stranded termini with their 3'–5'-exonucleolytic activities, and fill in recessed 3'-ends with their polymerizing activities.

The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., USA.

A desirable way to modify the DNA encoding the polypeptide of the invention is to use the polymerase chain reaction as disclosed by Saiki et al (1988) Science 239, 487–491.

In this method the DNA to be enzymatically amplified is flanked by two specific oligonucleotide primers which themselves become incorporated into the amplified DNA. The said specific primers may contain restriction endonuclease recognition sites which can be used for cloning into expression vectors using methods known in the art.

The present invention also relates to a host cell transformed with a polynucleotide vector construct of the present invention. The host cell can be either prokaryotic or eukaryotic. Bacterial cells are preferred prokaryotic host cells and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast and mammalian cells, preferably vertebrate cells such as those from a mouse, rat, monkey or human fibroblastic cell line. Yeast host cells include YPH499, YPHSO0 and YPHSO1 which are generally available from Stratagene Cloning. Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, and monkey kidney-derived COS-1 cells available from the ATCC as CRL 1650.

Transformation of appropriate cell hosts with a DNA construct of the present invention is accomplished by well-known methods that typically depend on the type of vector used. With regard to transformation of prokaryotic host cells, see, for example, Cohen et al (1972) *Proc. Natl. Acad. Sci. USA* 69, 2110 and Sambrook et al (1989) *Molecular Cloning, A Laboratory Manual*, Cold Spring Harbor Laboratory, Cold Spring Harbor, N.Y. Transformation of yeast cells is described in Sherman et al (1986) *Methods In Yeast Genetics, A Laboratory Manual*, Cold Spring Harbor, N.Y. The method of Beggs (1978) *Nature* 275, 104–109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA.

Electroporation is also useful for transforming cells and is well known in the art for transforming yeast cell, bacterial cells and vertebrate cells.

For example, many bacterial species may be transformed by the methods described in Luchansky et al (1988) Mol. Microbiol. 2, 637–646 incorporated herein by reference. The greatest number of transformants is consistently recovered following electroporation of the DNA-cell mixture suspended in 2.5× PEB using 6250V per cm at 25 µFD.

Methods for transformation of yeast by electroporation are disclosed in Becker & Guarente (1990) *Methods Enzymol.* 194, 182.

Successfully transformed cells, ie cells that contain a DNA construct of the present invention, can be identified by well-known techniques. For example, cells resulting from the introduction of an expression construct of the present invention can be grown to produce the polypeptide of the invention. Cells can be harvested and lysed and their DNA content examined for the presence of the DNA using a method such as that described by Southern (1975) *J. Mol. Biol.* 98, 503 or Berent et al (1985) *Biotech.* 3, 208. Alternatively, the presence of the protein in the supernatant can be detected using antibodies as described below.

In addition to directly assaying for the presence of recombinant DNA, successful transformation can be confirmed by well-known immunological methods when the recombinant DNA is capable of directing the expression of the protein. For example, cells successfully transformed with an expression vector produce proteins displaying appropriate antigenicity. Samples of cells suspected of being transformed are harvested and assayed for the protein using suitable antibodies. Thus, in addition to the transformed host cells themselves, the present invention also contemplates a culture of those cells, preferably a monoclonal (clonally homogeneous) culture, or a culture derived from a monoclonal culture, in a nutrient medium.

Thus, a second aspect of the invention provides a polynucleotide encoding a peptide of the invention.

A third aspect of the invention provides a vector comprising a polynucleotide of the invention and a fourth aspect of the invention provides a host cell comprising a polynucleotide or vector of the invention.

The compounds of the invention are useful in modulating cell migration and therefore are useful in medicine.

Thus, a fifth aspect of the invention provides a compound according to the first aspect of the invention for use in medicine.

A sixth aspect of the invention provides a pharmaceutical composition comprising a compound according to the first aspect of the invention and a pharmaceutically acceptable carrier.

The formulations may conveniently be presented in unit dosage form and may be prepared by any of the methods well known in the art of pharmacy. Such methods include the step of bringing into association the active ingredient (compound of the invention) with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavouring agents.

It is particularly preferred if the formulation is for topical administration, for example to the site of a wound.

It will be appreciated that some of the compounds of the invention will be in the form of salts.

Salts which may be conveniently used in therapy include physiologically acceptable base salts, for example, derived from an appropriate base, such as an alkali metal (e.g. sodium), alkaline earth metal (e.g. magnesium) salts, ammonium and $NX_4^+$ (wherein X is $C_{1-4}$ alkyl) salts. Physiologically acceptable acid salts include hydrochloride, sulphate, mesylate, besylate, phosphate and glutamate.

Salts according to the invention may be prepared in conventional manner, for example by reaction of the parent compound with an appropriate base to form the corresponding base salt, or with an appropriate acid to form the corresponding acid salt.

The aforementioned compounds of the invention or a formulation thereof may be administered by any conventional method including oral and parenteral (e.g. subcutaneous or intramuscular) injection. The treatment may consist of a single dose or a plurality of doses over a period of time.

Whilst it is possible for a compound of the invention to be administered alone, it is preferable to present it as a pharmaceutical formulation, together with one or more acceptable carriers. The carrier(s) must be acceptable in the sense of being compatible with the compound of the invention and not deleterious to the recipients thereof. Typically, the carriers will be water or saline which will be sterile and pyrogen free.

A further aspect of the invention provides a method of modulating cell migration the method comprising administering an effective amount of a compound according to the first aspect of the invention to the site where modulation of cell migration is required.

Preferred compounds are those preferred in the first aspect of the invention.

Cell migration may be modulated according to the method of this aspect of the invention in vitro, for example in cell culture systems, or it may be modulated in vivo.

Impaired cell migration is commonly a feature of clinical conditions in which wound healing is not optimal; the stimulation of cell migration under these conditions may prove beneficial. Conversely, elevated or inappropriate cell migration is a feature of several pathological conditions, including tumour invasion, pathological angiogenesis, inflammation and fibrosis. Inhibitors of IGD (SEQ ID NO 1) bioactivity may prove useful in the treatment of these conditions. Inhibitors of IGD (SEQ ID NO 1) bioactivity may be screened for using method apparent to the skilled person based on the information contained herein.

The modulation of cell migration is desirable in, for example, wound healing, guided periodontal tissue regeneration, inhibition of tumour invasion and metastasis, and the compounds of the invention are also useful because of their effects on angiogenesis (new blood vessel formation). The compounds of the invention may also be useful in relation to inflammation or connective tissue function.

Thus, it is preferred that the site where modulation of cell migration is in an animal body, for example a mammalian, especially human, body. It is also preferred if the cell whose migration is modulated is a fibroblast cell. We have shown that vascular cells are responsive to certain compounds of the invention (for example, IGDS), and that IGDS (SEQ ID NO 2) stimulates angiogenesis in the chick yolk sac assay. Thus, the compounds of the invention are believed to be clinically useful in stimulating angiogenesis in conditions such as impaired wound healing.

It will be seen, therefore, that the invention includes a method of treating an animal, for example a mammal, especially human, in need of modulation of cell migration the method comprising administering to the animal an effective amount of a compound according to the first aspect of the invention.

A further aspect of the invention provides the use of a compound of the invention for modulating cell migration, especially in wound healing or periodontal tissue regeneration or inhibition of tumour invasion and metastasis or in modulating angiogenesis.

A still further aspect of the invention therefore provides use of a compound of the invention in the manufacture of a medicament for modulating cell migration in an animal body.

BRIEF DESCRIPTION OF THE DRAWINGS

Detailed description of the preferred embodiment of the invention will be made with reference to the accompanying drawings.

FIG. 5 is the primary amino acid structure of human fibronectin (SEQ ID NO 7);

DETAILED DESCRIPTION OF THE PREFERRED EMBODIMENT

Figure 1:
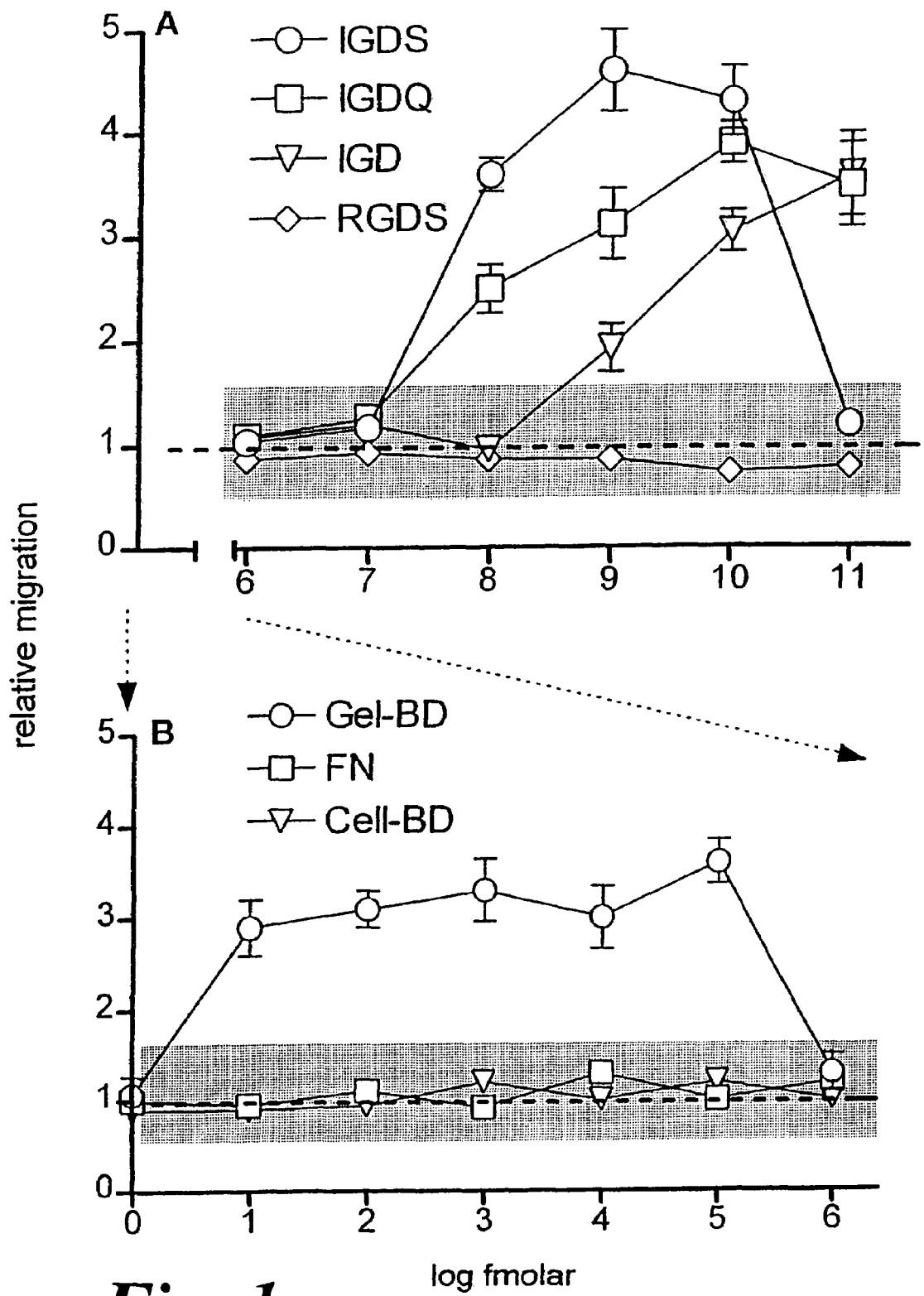
FIGS. 1A (top) and 1B (bottom) are graphs showing the effects of synthetic peptides and fibronectin domains on cell migration in the native collagen gel assay.

The invention will now be described in more detail with reference to the following Figures and Examples in which:

FIG. 1 shows the effects of synthetic peptides and fibronectin domains on cell migration in the native collagen gel assay. Assays were performed as described in Materials and Methods in Example 1. Results are normalised by expressing them as "relative stimulation" of migration, this being calculated by dividing the percentage of cells in the gel matrix for each experimental point by the control value obtained in that particular experiment. Data are presented as the mean ±SD of five experiments. For clarity, the shaded area indicates the spread of standard deviations for data points not plotted with error bars. Upper panel: results obtained with the indicated synthetic peptides. Lower panel: results obtained with native fibronectin (FN), and its cell-binding (Cell-BD) and gelatin-binding (Gel-BD) domains.

Figure 2:
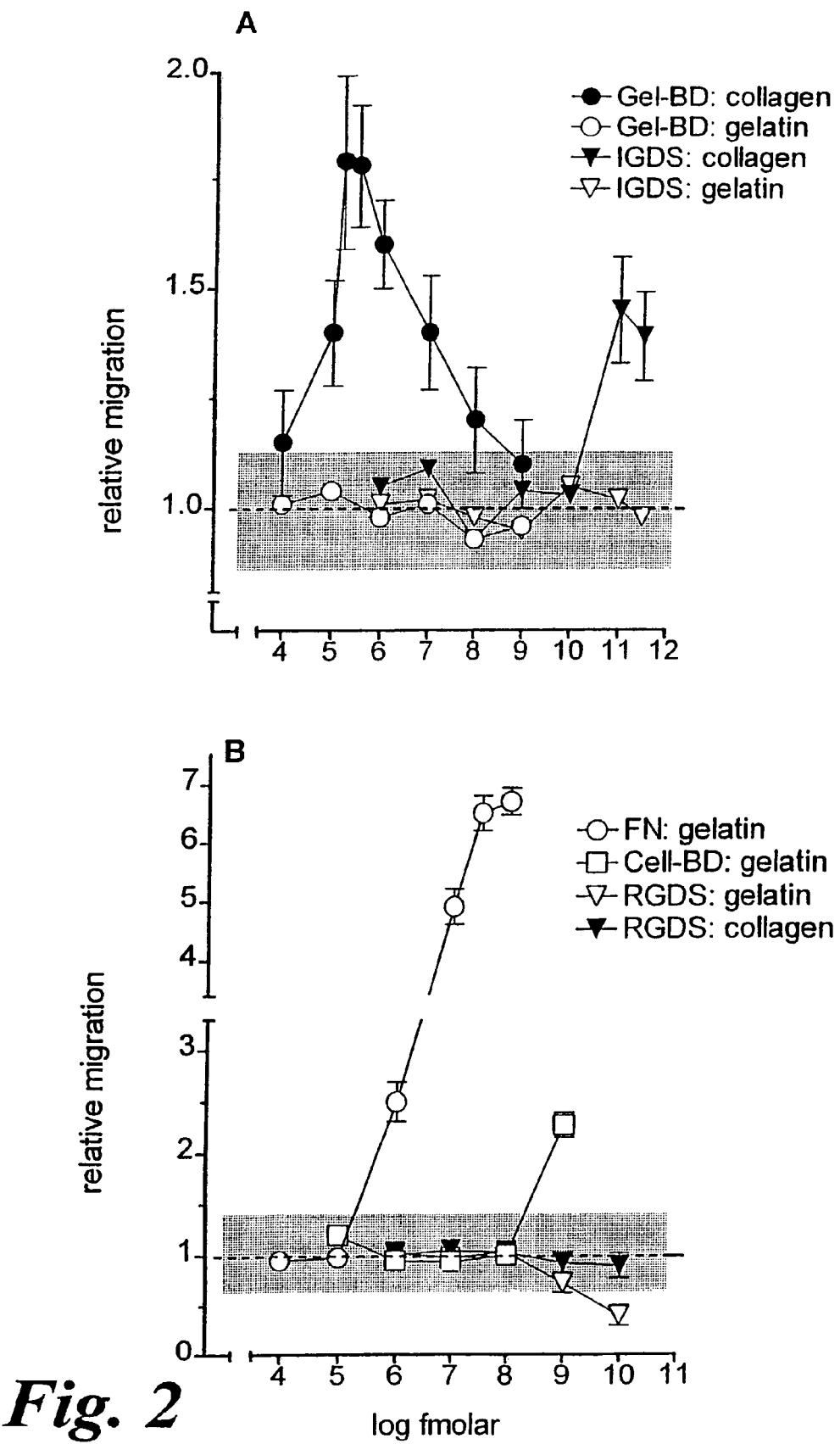
FIGS. 2A (top) and 2B (bottom) are graphs showing the effects of synthetic peptides and fibronectin domains on cell migration in the transmembrane assay.

FIG. 2 shows the effects of synthetic peptides and fibronectin domains on cell migration in the transmembrane assay. Assays were performed as described in Materials and Methods in Example 1. Results from five experiments are presented as mean ±SD. Shaded area indicates the spread of standard deviations for data points not plotted with error bars. Panel A: results obtained with IGDS (SEQ ID NO 2) and the gelatin-binding domain (Gel-BD) on membranes coated with native collagen and gelatin. Panel B: results obtained with RGDS (SEQ ID NO 6), native fibronectin (FN), and its cell-binding domain (Cell-BD).

Figure 3:
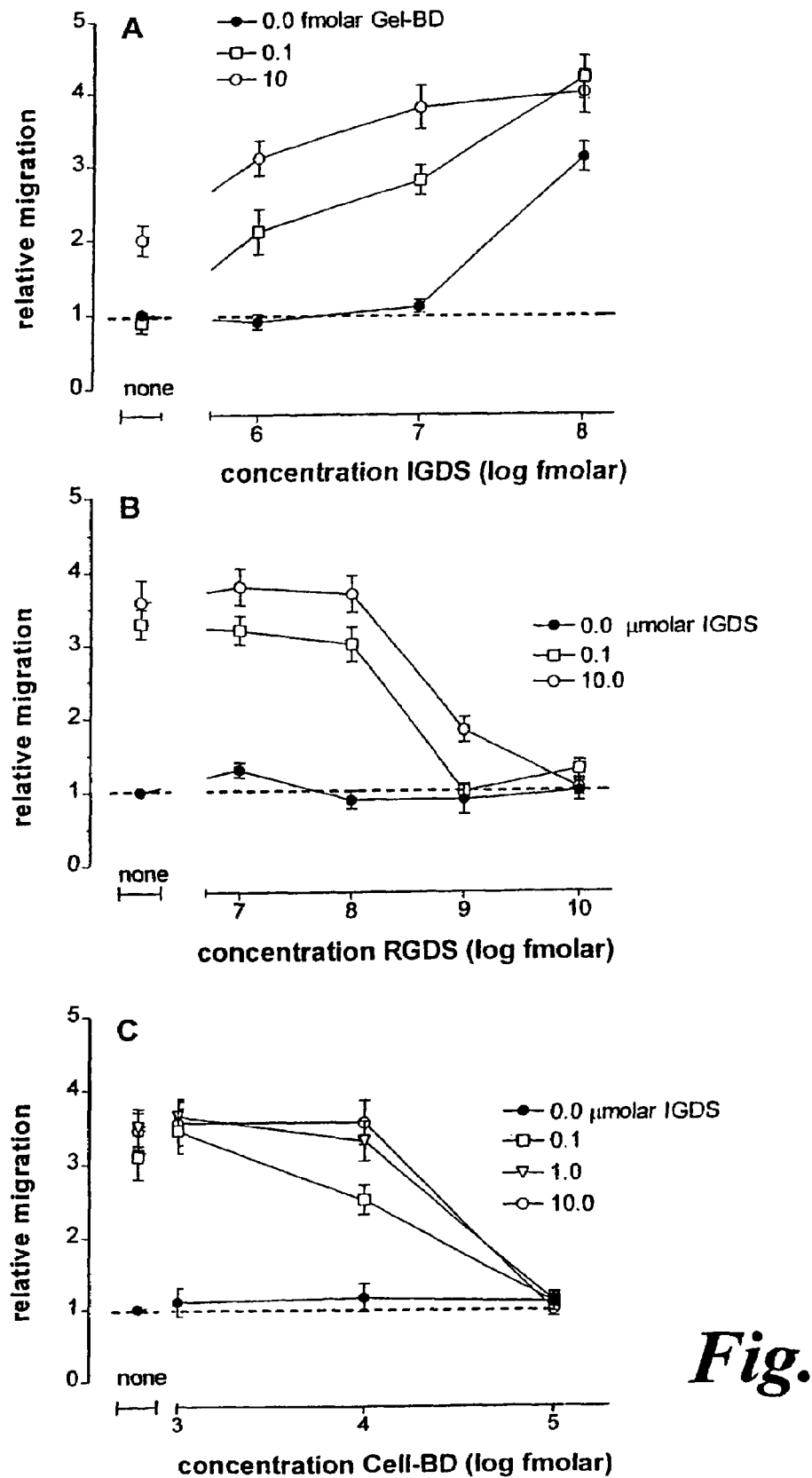
FIGS. 3A (top), 3B (middle) and 3C (bottom) are graphs showing the effects of different peptides on the migration of stimulating activity of the gelatin-binding domain of fibronectin and IGDS (SEQ ID NO 2)

FIG. 3 shows the effect of different peptides on the migration of stimulating activity of the gelatin-binding domain of fibronectin and IGDS (SEQ ID NO 2). The collagen gel assay was performed in the presence of various combinations of the indicated peptides and the percentage of cells present within the gel matrix measured after a four-day incubation period. Data are expressed as mean ±SD obtained in three experiments. Panel A: combinations of the gelatin-binding domain (Gel-BD) and IGDS (SEQ ID NO 2); Panel B: combinations of IGDS (SEQ ID NO 2) and RGDS (SEQ ID NO 6); Panel C: combinations of IGDS (SEQ ID NO 2) and the cell-binding domain (Cell-BD).

Figure 4:
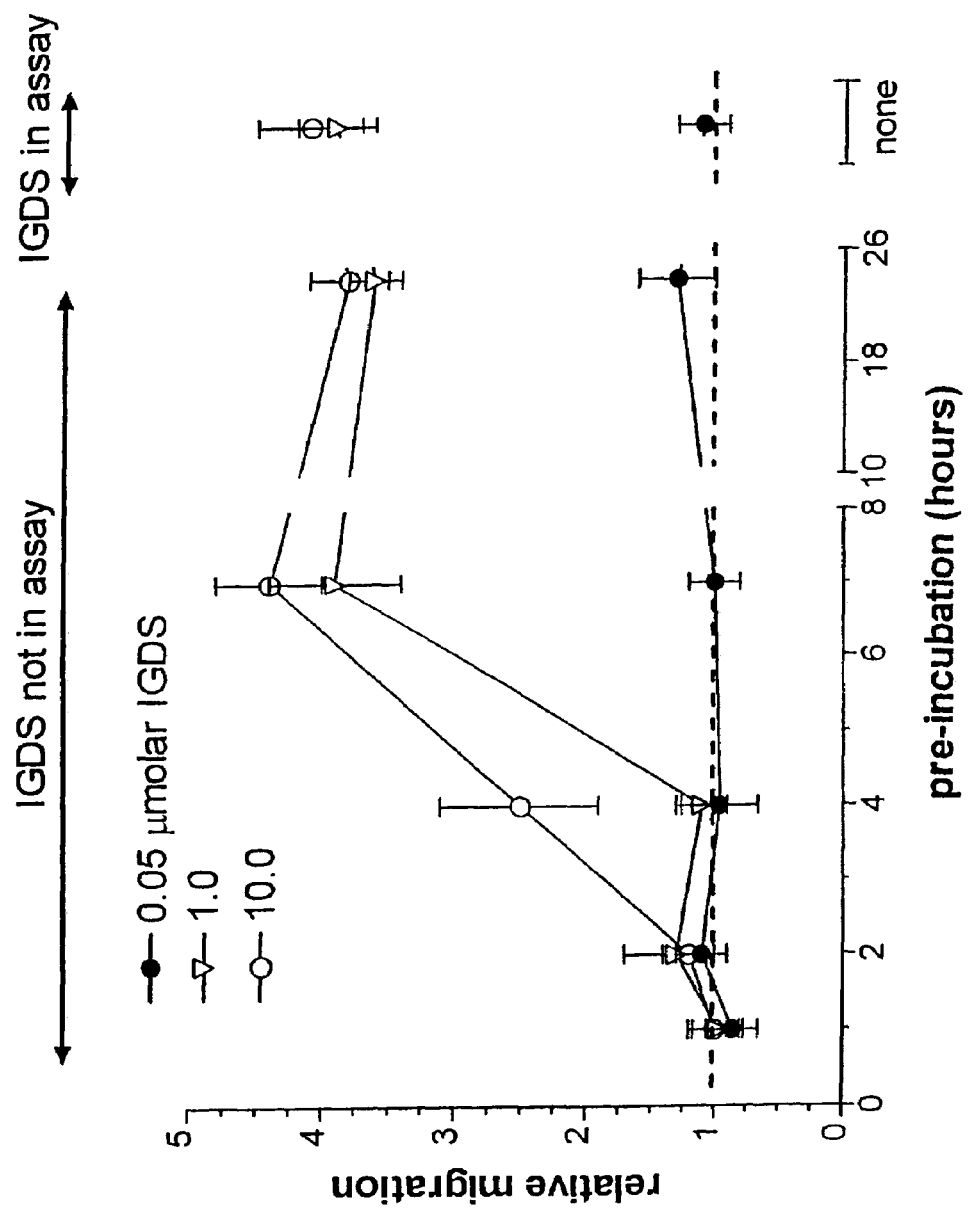
FIG. 4 is a graph showing the effects of pre-incubation of cells with synthetic peptides on their subsequent migration in the native collagen gel assay.

FIG. 4 shows the effect of pre-incubation of cells with synthetic peptides on their subsequent migration in the native collagen gel assay. Confluent cells on plastic tissue culture dishes were washed 3× with serum-free MEM (SF-MEM) and then incubated for various times with the indicated concentrations of IGDS (SEQ ID NO 2) in SF-MEM. They were then trypsinised and washed extensively by repeated (5×) cycles of centrifugation and resuspension in SF-MEM. The behaviour of these pre-incubated cells was assessed in the collagen gel assay in the absence of further IGDS (SEQ ID NO 2)(indicated as IGDS (SEQ ID NO 2) not in assay). These results were compared with the response of control cells to IGDS (SEQ ID NO 2) present during the four-day duration of the migration assay (indicated as IGDS (SEQ ID NO 2) in assay). Data were obtained from three experiments and are expressed as mean ±SD.

FIG. 5 shows the primary amino acid structure of human fibronectin.

Primary structure of Fibronectin

| | | | |
|---|---|---|---|
| Ala A 100 | Cys C 63 | Asp D 126 | Glu E 145 |
| Phe F 54 | Gly G 208 | His H 51 | Ile I 121 |
| Lys K 78 | Leu L 136 | Met M 27 | Asn N 101 |
| Pro P 195 | Gln Q 133 | Arg R 126 | Ser S 200 |
| Thr T 268 | Val V 200 | Trp W 40 | Tyr Y 105 |
| Mol. Wt (calc.) = 273 715 | | Residues = 2476 | |

Structural sites
Signal peptide: 1–20
Propeptide: 21–31
Type I repeats: 52–96, 97–140, 141–185, 186–230, 231–272, 308–344, 470–517, 518–560, 561–608, 2297–2341, 2342–2385, 2386–2428
Type II repeats: 345–404, 405–469
Type III repeats: 609–700, 719–809, 810–905, 906–995, 996–1085, 1086–1172, 1173–1265, 1357–1447, 1448–1537, 1538–1631, 1632–1721, 1812–1903-, 1904–1992, 1993–2082, 2203–2273
Alternatively spliced domains: 172–1811 (ED-A), 1266–1356 (ED-B), 2083–2202 (IIICS)
Potential N-linked glycosylation sites: 430, 528, 542, 877, 1007, 1244, 1291, 15 1904, 2199
O-Linked glycosylation site: 2155
Interchain disulphide bond residues: 2458, 2462
RGDD (SEQ ID NO 13) cell adhesion site: 1615–1618
(DAPS(SEQ ID NO 8) cell adhesion site: 1994–1998
LDV (SEQ ID NO 9) cell adhesion site: 2102–2104
REDV (SEQ ID NO 10) cell adhesion site: 2182–2185
Heparin-binding sites: 2028–2046 (FN-C/H I), 2068–2082 (FN-C/H II)
Factor XIIIa transglutaminase cross-linking site: 34

Figure 6:
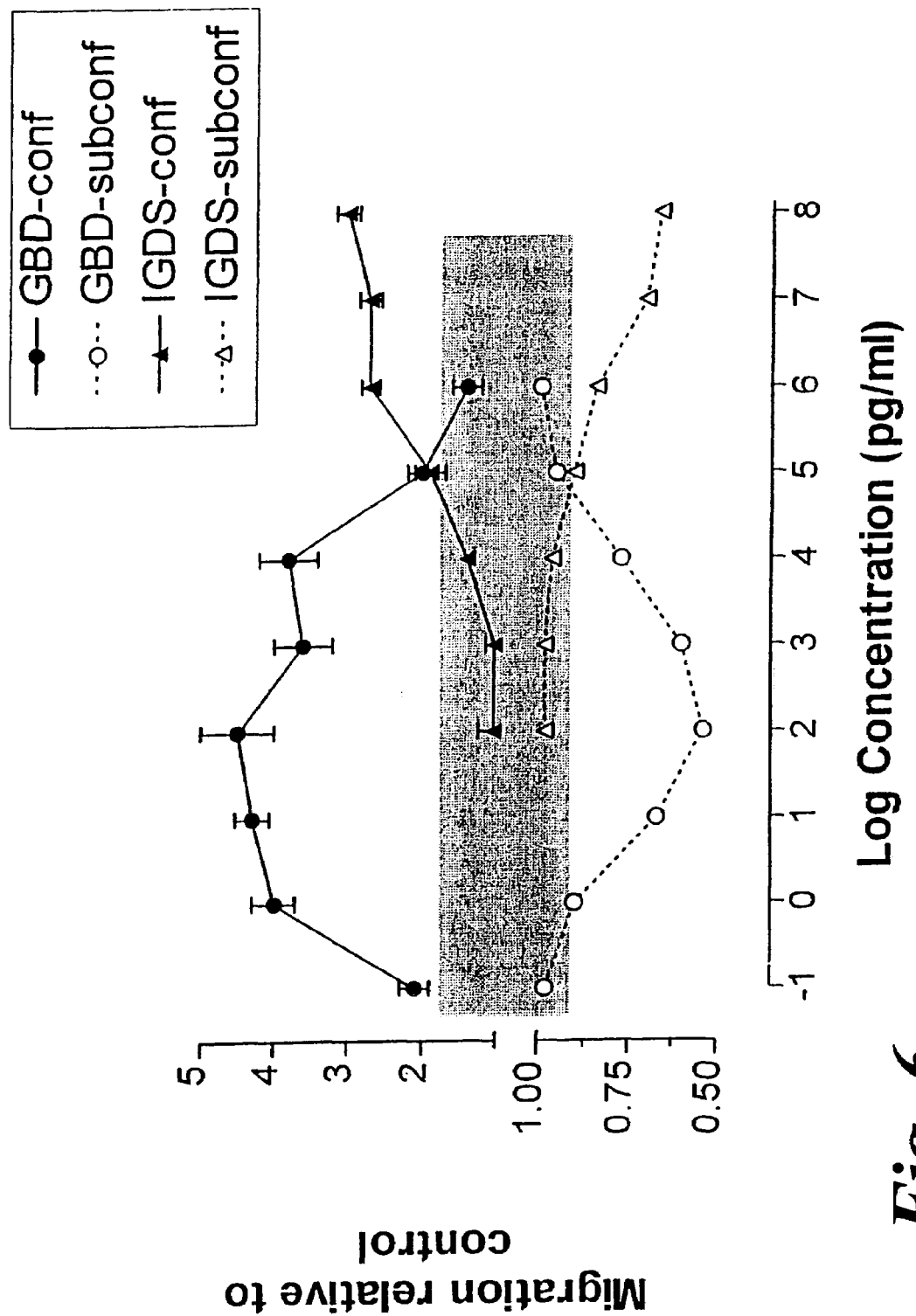
FIG. 6 is a graph showing the modulation of the effect of GBD and the IGDS (SEQ ID NO 2) tetrapeptide on fibroblast migration into 3D collagen matrices by cell density.

FIG. 6 shows the modulation of the effect of GBD and the IGDS (SEQ ID NO 2) tetrapeptide on fibroblast migration into 3D collagen matrices by cell density. Cells were plated at either confluent (conf) or subconfluent (subconf) densities. Shaded area indicates range of control values.

Figure 7:
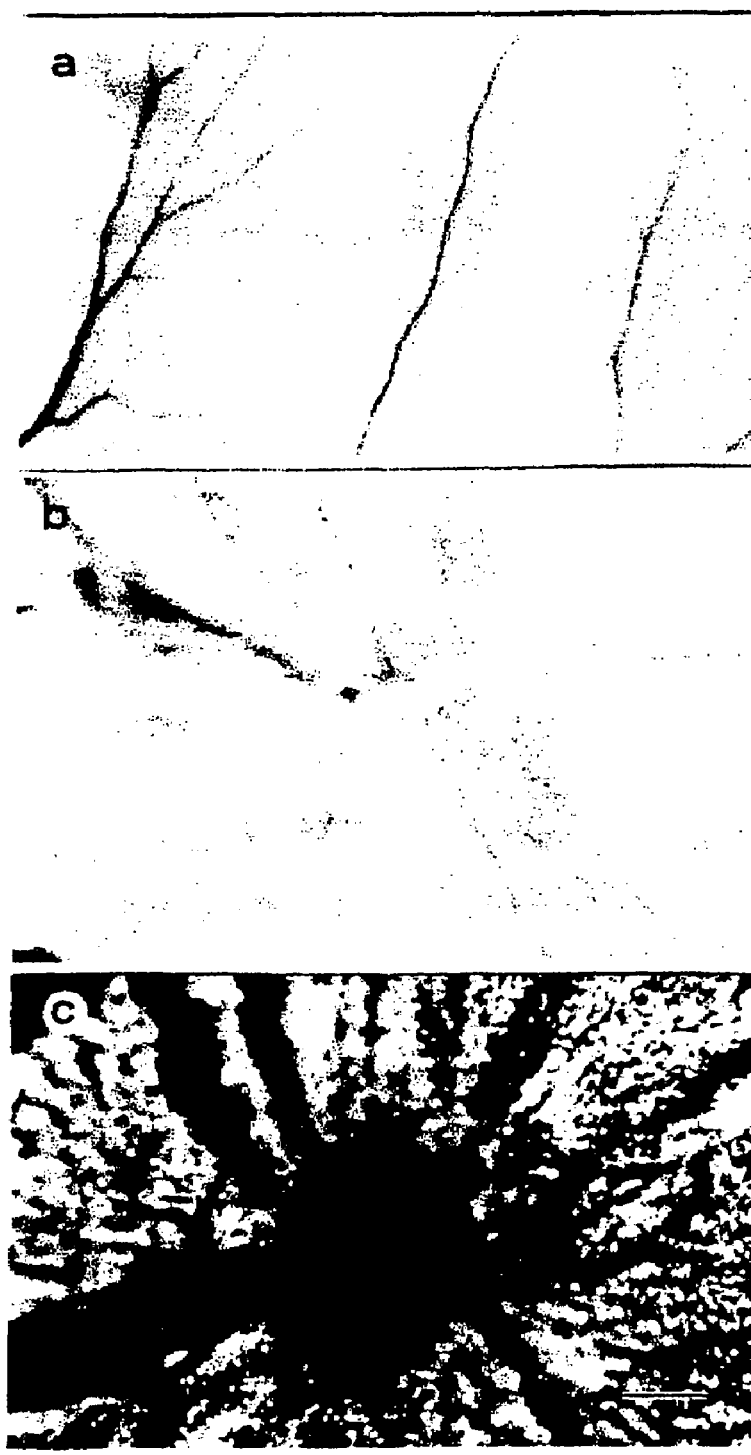
FIG. 7 (top and bottom) are photomicrographs of the angiogenic activity 15 of IGDS (SEQ ID NO 2) synthetic peptide and gelatin-binding domain of fibronectin in the chick yolk sac membrane assay.

FIG. 7 shows the angiogenic activity of IGDS (SEQ ID NO 2) synthetic peptide and gelatin-binding domain of fibronectin in the chick yolk sac membrane assay. Dried methylcellulose pellets containing the test samples and control pellets (lacking the test samples) were placed on the yolk sac membrane of 6-day chick embryos, as described in Materials and Methods in Example 1. The elicited reaction was checked after six hours and assessed after 24 hr by observation of living embryos with a stereomicroscope. A. negative angiogenic response (in this case, elicited by control pellet); B. typical positive angiogenic response (in this case, elicited by pellet containing 1.0 µg IGDS (SEW ID NO 2)). After assessment at 24 hr, selected membranes were fixed in 2.5% EM grade glutaraldehyde in 0.2 M phosphate buffer, pH 7.4. These preparations were then stained with 1% toluidine blue and photographed using a Leica DM LB microscope. C. appearance of fixed and stained positive angiogenic response (in this case, elicited by pellet containing 1.0 µg of the gelatin-binding domain). Bar=250 µm.

EXAMPLE 1

Migration Stimulating Activity of the IGD (SEQ ID NO 1) Amino Acid Motif

Summary

The gelatin-binding domain of fibronectin stimulates fibroblast migration into matrices of native type I collagen, but is devoid of such activity with cells adherent to a denatured collagen substratum. We now demonstrate the IGD (SEQ ID NO 1) motif, present at two sites within the gelatin-binding domain, displays the same substratum-dependent activity. Micromolar concentrations of IDG-containing synthetic peptides stimulated fibroblast migration into native (but not denatured) collagen substrata in the following activity order: IGDS (SEQ ID NO 2)>IGDQ (SEQ ID NO 3)>IGD (SEQ ID NO 1). The related RGDS (SEQ ID NO 6) peptide did not affect cell migration on its own and inhibited the bioactivity of IGDS (SEQ ID NO 2) in a dose-dependent fashion. Cells pre-incubated with IGDS (SEQ ID NO 2) displayed a persistent stimulation of cell migration when assayed in the absence of further IGDS. This feature of IGDS (SEQ ID NO 2) bioactivity provided a means to study the early events of IGDS (SEQ ID NO 2) action (for example, receptor ligation and post-ligation signalling) separately from the late events resulting in the persistent stimulation of cell migration. Accordingly, experiments in which cells were incubated with IGDS (SEQ ID NO 2) and inhibitors in various temporal combinations indicated that (a) both early and late events of IGDS (SEQ ID NO 2) action were effectively inhibited by RGDS, as well as function-blocking antibodies to integrin subunits ($\beta_1$ and $\beta_3$) and heterodimer $\alpha_v\beta_3$, (b) neutralising antibodies to the classic fibronectin-binding $\alpha_5\beta_1$, integrin were without effect, and (c) inhibition of tyrosine kinase activity blocked early events of IGDS (SEQ ID NO 2) action, inhibition of MAP kinase kinase blocked both early and late events, whilst inhibition of PKA only affected late events. In vivo studies further indicated that IGDS (SEQ ID NO 2) synthetic peptide elicited an angiogenic response in the chick yolk sac membrane; in contrast, RGDS (SEQ ID NO 6) and RGES (SEQ ID NO 11) peptides were inactive under the same experimental conditions. The expression of biological activity by IDG (SEQ ID NO 1) synthetic peptides (both in vitro and in vivo) stands in marked contrast to the inactivity of their well-studied RGDS (SEQ ID NO 6) counterparts and opens the possibility of developing a novel family of clinically relevant agents.

Materials and Methods

Chemicals. The synthetic peptides were prepared to greater than 99% purity in the Department of Biochemistry, University of Dundee. Fibronectin and its cell-binding and gelatin-binding domains were purified as previously described[7]. Monoclonal antibodies to the integrin subunits $\alpha2$ (cat. no. MCA743) and $\beta1$ (MCA1188) were supplied by Serotec (Oxford, UK); antibodies to $\beta3$ (MAB1957), $\alpha v\beta3$ (MAB1976) and $\alpha5\beta1$ (MAB 1969) were supplied by Chemicon (Harrow, UK); antibody to $\alpha5\beta1$ (M0604) was supplied by Dako (High Wycombe, UK). Genistein (cat. no. 34583-Q) and PD98059 (cat. no. 178278-Q) were purchased from Calbiochem, Nottingham. PKA inhibitor peptide (cat. no. P6062) was purchased from Sigma Chemical Co (Poole, Dorset, UK).

Cells. Experiments were performed with two lines of human skin fibroblasts (SK319 and FSF44, between passage 10–18) shown to be free of mycoplasmal contamination by staining with Hoechst 33256. Identical results were obtained with both lines and these cells are consequently not individually identified in the Figures. Stock cultures were maintained in Eagle's Minimal Essential (MEM), as previously described[7].

Migration Assays. In the collagen gel assay, pre-formed 2 ml gels were overlaid with 1 ml of serum-free MEM (controls) or serum-free MEM containing the requisite concentration of effector molecule to give the desired final concentration. Trypsinised fibroblasts were suspended in serum-free MEM to give an inoculum containing $2\times10^5$ cells/ml and 1 ml of this was plated onto replicate control and test gels. After a 4-day incubation period at 37° C., the cells on the surface and within the 3D matrix of the gel were counted in 15 randomly selected fields by microscopic observation and these data used to calculate the percentage of total cells present within the gel matrix[6].

Polycarbonate membranes used in the transmembrane assay were immersed in an aqueous solution containing 10 μg/ml of either native type I collagen or heat-denatured type I collagen (gelatin) overnight at 37° C. and then air-dried. Assays were performed as previously described[7].

Chick yolk sac membrane angiogenesis assay. The assay was performed essentially as described by Gush et al (1990) *J. Med. Engineer. Tech.* 14, 205–209. Accordingly, four-day-old fertilised eggs were cracked in a tumbler, covered with a Petri dish and incubated at 37° C. Two days later dried methylcellulose pellets containing the test samples and control pellets (lacking the test samples) were placed on the yolk sac membrane. The elicited angiogenic reaction was assessed after 24 hr by observation of living embryos with a stereomicroscope. Selected membranes were fixed in 2.5% EM grade glutaraldehyde in 0.2 M phosphate buffer (pH 7.4), dissected, stained with 1% toluidine blue and mounted on glass slides for photomicroscopy.

Results and Discussion

Inspection of the amino acid sequence of the gelatin-binding domain revealed that it contains two IGD (SEQ ID NO 1) motifs located in the seventh and ninth type I repeat modules, respectively. This is of particular interest, as the IGD (SEQ ID NO 1) motif is a highly conserved feature of the type I module[8] and its location at the apex of the main type I loop is homologous to that of the RGD (SEQ ID NO 4) motif in the tenth type III repeat[9]. Relevant IGD-containing synthetic peptides were synthesised and their effect on the migration of human dermal fibroblasts examined in the collagen gel assay. Results summarised in FIG. 1A indicate that IGDS (SEQ ID NO 2)(as present in the ninth type I module), IGDQ (SEQ ID NO 3)(as present in the seventh type I module) and IGD (SEQ ID NO 1) stimulated cell migration into native type I collagen gels in a dose-dependent fashion. Significant bioactivity was expressed by IGDS (SEQ ID NO 2) and IGDQ (SEQ ID NO 3) at a concentration of 0.1 μM, whilst comparable activity was first manifest by IGD (SEQ ID NO 1) at 10–100 μM. IGDS (SEQ ID NO 2) produced a bell-shaped dose-response; this was not obtained with either IGDQ (SEQ ID NO 3) or IGD (SEQ ID NO 1) within the concentration range examined. The structurally related RGDS (SEQ ID NO 6) tetrapeptide was devoid of migration stimulating activity in the native collagen gel assay. Comparative results obtained with purified, proteolytically-generated, fibronectin fragments (FIG. 1B) confirmed our previous observations that the gelatin-binding domain exhibits significant migration stimulating activity, whilst native fibronectin and its purified cell-binding domain are inactive when tested within the same concentration range[7]. Comparison of data presented in FIGS. IA and B further indicate that the micromolar concentration range of IGD (SEQ ID NO 1)-containing synthetic peptides required to induce a stimulation of cell migration is many orders of magnitude greater than the corresponding femtomolar concentration range of the larger gelatin-binding domain.

These observations suggest the involvement of other amino acid motifs within the gelatin-binding domain in facilitating recognition and/or binding of IGD (SEQ ID NO 1) to its putative cell surface receptor. In this context, Aota et al[10] reported that the PHSRN (SEQ ID NO 12) sequence in the ninth type III module of the cell binding domain is such a "synergistic" motif for RGD-dependent biological activity.

The effects of a native and denatured type I collagen substratum on the migration stimulating activity of IGD-containing synthetic peptides was assessed in the transmembrane assay. Data presented in FIG. 2A indicate that IGDS (SEQ ID NO 2) stimulated cell migration through membranes coated with native collagen, but was devoid of activity on gelatin-coated membranes. Similar results were obtained with IGDQ (SEQ ID NO 3) and IGD (SEQ ID NO 1)(data not shown). These observations indicate that the bioactivity of IGD-containing synthetic peptides is (a) dependent upon cell attachment to a native collagen substratum, and (b) resembles that of the larger gelatin-binding domain in which it is contained in terms of this criterion. The mechanism responsible for the substratum-dependent nature of IGD (SEQ ID NO 1) activity remains to be determined. In this regard, it may be relevant that cellular adhesion to a native collagen substratum specifically affects a number of cellular processes of potential relevance to the modulation of cell migration (for example, phosphorylation of pp125FAK and activation of PKC-ζ)[11,12].

Data presented in FIG. 2B confirm that native fibronectin and its purified cell binding domain stimulate cell migration through membranes coated with gelatin (as reported in previous studies) and that the RGDS (SEQ ID NO 6) synthetic peptide is inactive on both collagen- and gelatin-coated membranes.

The possible mechanistic relationship between IGDS (SEQ ID NO 2) and the gelatin-binding domain in which it is contained was further examined by co-incubating cells with suboptimal concentrations of each. The results presented in FIG. 3A indicate that these two peptides exerted an additive effect upon cell migration, consistent with the hypothesis that the IGD (SEQ ID NO 1) motif within the gelatin-binding domain is indeed responsible for its stimulation of cell migration. This additive effect was particularly apparent at 0.1 fM GBD and 0.01 μM ($10^7$ fM) IGDS, which were each inactive when present on their own, but active in combination.

Possible mechanistic interactions between IGDS (SEQ ID NO 2) and RGDS (SEQ ID NO 6) were studied in similar co-incubation experiments. Results presented in FIG. 3B indicate that RGDS (SEQ ID NO 6) effectively inhibited the migration stimulating activity of IGDS (SEQ ID NO 2). The cell-binding domain of fibronectin (which contains the RGDS (SEQ ID NO 6) motif also inhibited IGDS (SEQ ID NO 2) activity (FIG. 3C). As expected, the inhibition of IGDS (SEQ ID NO 2) activity was achieved at considerably lower (nanomolar) concentrations of the cell-binding domain compared to the pmolar concentrations required of RGDS (SEQ ID NO 6). The RGES (SEQ ID NO 11) synthetic peptide had no effect on IGDS (SEQ ID NO 2) migration stimulating activity when tested at the same concentration range as RGDS (SEQ ID NO 6)(data not shown).

A number of biological activities of fibronectin are "cryptic" in the sense that they are displayed by fibronectin proteolytic fragments, but not by the intact molecule[5,13]. Fukai et al[14] have demonstrated that the expression of these cryptic activities require either the denaturation of native fibronectin and/or its limited proteolytic degradation into functional domains in order to become manifest. These authors suggest that relaxation of steric hindrance may be responsible for the unmasking of latent biological activity by these procedures. The inhibition of IGDS (SEQ ID NO 2)-induced cell migration by the RGDS (SEQ ID NO 6) amino acid motif may provide an additional mechanism for the apparent lack of IGDS (SEQ ID NO 2) activity in native fibronectin (FIG. 1 B).

We have previously reported that cells pre-incubated for 24 hr with the gelatin-binding domain of fibronectin displayed elevated migratory activity when subsequently plated on native collagen gels in its absence[7]. Data presented in FIG. 4 indicate that the effect of IGDS (SEQ ID NO 2) on cell migration is similarly persistent, exhibiting a dependence upon both the time of pre-incubation and peptide concentration. This elevated migratory behaviour is still manifest by pre-incubated cells following 1–2 passages in vitro (data not shown).

The persistence of IGDS (SEQ ID NO 2)-bioactivity suggests that its mode of action involves a series of early events which are dependent upon the presence of IGDS (SEQ ID NO 2)(such as receptor ligation and post-ligation signalling) and later events, which no longer require the presence of IGDS (SEQ ID NO 2) and ultimately result in stabilisation of a persistent migratory phenotype. The specific effects of potential inhibitory molecules on such early and late events were examined by using the following experimental protocol: (a) pre-incubating cells with IGDS (SEQ ID NO 2) and inhibitor and then assaying these treated cells in the absence of both IGDS (SEQ ID NO 2) and inhibitor (note: this protocol provides data concerning the effects of inhibitor on the early events mediating IGDS (SEQ ID NO 2) activity), (b) pre-incubating cells with neither IGDS (SEQ ID NO 2) nor inhibitor and assaying them in the presence of both (the effects of inhibitor on both early and late events), (c) pre-incubating cells with IGDS (SEQ ID NO 2) alone and then assaying them in the presence of inhibitor only (the effects of inhibitor on late events), and finally, (d) pre-incubating cells with inhibitor alone and then assaying them in the presence of IGDS (SEQ ID NO 2) to provide control information regarding possibly persistent effects of inhibitor which would confound data interpretation. Data presented in Table IA are concerned with the effects of the synthetic RGDS (SEQ ID NO 6) and RGES (SEQ ID NO 5). Our results indicate that RGDS (SEQ ID NO 6) inhibited both IGDS (SEQ ID NO 2) cell signalling and subsequent cell migration. RGES (SEQ ID NO 11) was inactive under all experimental conditions. Control data (protocol "d") indicated that both peptides had no persistent effect on IGDS (SEQ ID NO 2) activity; all of the other inhibitors examined were similarly devoid of such potentially confounding activity (data not shown).

The inhibitory effects of RGDS (SEQ ID NO 6) on IGDS-induced cell migration may occur by competition for receptor ligation. In order to obtain data relevant to this possibility, we employed the above pre-incubation protocols to examine the effects of neutralising antibodies to several integrins expressed by human dermal fibroblasts in vitro[15]

Our data indicate that the monoclonal antibody recognising the a2 integrin subunit inhibited cell migration induced by IGDS (SEQ ID NO 2), but did not affect initial IGDS (SEQ ID NO 2) signalling (Table 3B). This observation is consistent with the role of α2β1 in mediating cell attachment to collagen and its involvement in supporting cell migration on this substratum[16]. Antibodies to the αvβ3 heterodimer, as well as to the integrin subunits α1 and β3, were found to block both the initial events of IGDS (SEQ ID NO 2) signalling and subsequent cell migration. The αvβ3 heterodimer recognises the RGDS (SEQ ID NO 6) motif, whilst the β₁ and β₃ subunits are present in several integrin heterodimers which also recognise RGDS[15,17]. Several previous studies have implicated these integrins in the mediation of cell migration[16,18]. In this context, it should be noted that the α_vβ_3 heterodimer also binds to exposed RGD (SEQ ID NO 4) sites in denatured (but not native) collagen[19]; this differential ligation of denatured and native type I collagen by α_vβ_3 may contribute to the substratum-dependent nature of fibroblast migratory response to IGD-containing peptides reported here. Two antibodies to the "classic" fibronectin-binding α₅β₁ integrin had no effect on IGDS-induced cell migration (Table 3B). These observations are consistent with previous reports suggesting that integrin α₅β₁ preferentially mediates cell adhesion rather than migration[20]. Recent studies have underscored the interplay between substratum, ligand concentration and integrin function in the control of cell migration[21,22]; these complex factors will need to be taken into account in identifying the precise integrin receptors involved in IGD (SEQ ID NO 1) ligation and the post-ligation events leading to the resultant substratum-dependent biological activity.

Results obtained with signal transduction inhibitors indicate that the tyrosine kinase inhibitor *Genistein* selectively blocked IGDS (SEQ ID NO 2)-induced cell signalling, but did not affect cell migration (Table 1C). This finding is consistent with the role of focal adhesion-associated tyrosine kinases (such as pp125FAK) in mediating integrin signal transduction[23]. The MAP kinase kinase inhibitor PD98059 blocked both signal transduction and cell migration, in keeping with the previously reported activation of the MAP kinase cascade by integrin ligation[24]. In contrast, the PKA inhibitor blocked cell migration, but did not appear to affect initial IGDS (SEQ ID NO 2)-dependent events.

In addition to RGD, other amino acid sequences in fibronectin have been reported to mediate cell adhesion and migration; these include LDV (SEQ ID NO 9), REDV (SEQ ID NO 9) and IDAPS (SEQ ID NO 8)[17]. All these motifs resemble RGD (SEQ ID NO 4) in that migration stimulating activity is not retained by the respective soluble synthetic peptides. The migration-stimulating activity of IGD-containing synthetic peptides appears to be unique in this sense. Although biological activity has not previously been ascribed to the conserved IGD (SEQ ID NO 1) motif in fibronectin, previous studies have implicated the ninth type I repeat (which contains the IGDS (SEQ ID NO 2) sequence in the assembly of an extracellular fibronectin matrix[25]. The data presented here may be relevant in this context and suggest several integrins which may function in IGDS (SEQ ID NO 2) ligation.

The migration inhibiting activity of RGD-containing peptides has a number of potential clinical applications[26,27]. Structure-function studies have indicated that conservative and non-conservative amino acid substitutions, tandem amino acid extensions and cyclicisation significantly modulate the biological activity of the RGD (SEQ ID NO 4) motif in these situations[28,29]. The converse migration-stimulating activity of IGD (SEQ ID NO 1)-containing synthetic peptides may provide an analogous platform for developing a new family of therapeutic agents which promote cell migration in clinically relevant conditions, such as impaired wound healing.

EXAMPLE 2

Angiogenic Response in a Rat Wound Healing Model

The IGDS (SEQ ID NO 2) peptide has been shown to stimulate fibroblast migration and elicit and angiogenic response in a rat wound healing model. In this experimental system, 1 cm² pieces of porcine dermal collagen films impregnated with either control medium or medium containing the indicated concentration of test substance were implanted subcutaneously into rats. The animals were sacrificed 28 days later and the removed collagen implants fixed and sectioned for image analysis. The following data were obtained, indicating that IGDS (SEQ ID NO 2) stimulated both fibroblast migration into the collagen film and an angiogenic response.

|  | Vessels (per field) | Fibroblasts (% field) |
|---|---|---|
| Control | 15.3 ± 5.5 | 8.3 ± 6.7 |
| IGDS (1 µg/ml) | 26.7 ± 6.4 | 18.2 ± 9.4 |
|  | p < 0.01 | p < 0.01 |

TABLE 3

Effects of various inhibitors on early (receptor ligation and signalling) and late persistent stimulation of cell migration) aspects of IGDS (SEQ ID NO 2) activity.

A: synthetic peptides

| Peptide (µ molar) | Pre-incubation IGDS | Pre-incubation Peptide | In assay IGDS | In assay peptide | % inhibition | Inhibitory activity yes(+) no(−) |
|---|---|---|---|---|---|---|
| RGDS (10.0) | − | − | + | + | 92.3 ± 2.1 | early events: + |
|  | + | + | − | − | 96.2 ± 4.8 | late events: + |
|  | + | − | − | + | 96.5 ± 5.7 |  |
| RGES (10.0) | − | − | + | + | 1.2 ± 2.1 | early events: − |
|  | + | + | − | − | −1.0 ± 3.0 | late events: − |
|  | + | − | − | + | 0.3 ± 2.8 |  |

B: integrin antibodies

| Antibody (µg/ml) | Pre-incubation IGDS | Pre-incubation antibody | In assay IGDS | In assay antibody | % inhibition | Inhibitory activity yes(+) no(−) |
|---|---|---|---|---|---|---|
| α₂ (10.0) | − | − | + | + | 92.9 ± 6.1 | early events: − |
|  | + | + | − | − | −5.7 ± 2.0 | late events: + |
|  | + | − | − | + | 97.4 ± 8.9 |  |
| β₁ (10.0) | − | − | + | + | 96.1 ± 2.1 | early events: + |
|  | + | + | − | − | 92.8 ± 3.9 | late events: + |
|  | + | − | − | + | 99.1 ± 5.5 |  |
| β₃ (10.0) | − | − | + | + | 94.0 ± 4.2 | Early events: + |
|  | + | + | − | − | 98.0 ± 1.0 | Late events: + |
|  | + | − | − | + | 96.7 ± 3.6 |  |
| α₅β₁ (10.0) | − | − | + | + | 4.1 ± 3.3 | Early events: − |
|  | + | + | − | − | 3.6 ± 2.8 | Late events: − |
|  | + | − | − | + | −0.1 ± 2.6 |  |
| α_vβ_3 (10.0) | − | − | + | + | 97.9 ± 4.7 | Early events: + |
|  | + | + | − | − | 88.0 ± 3.3 | Late events: + |

TABLE 3-continued

Effects of various inhibitors on early (receptor ligation and signalling) and late persistent stimulation of cell migration) aspects of IGDS (SEQ ID NO 2) activity.

| | | | | |
|---|---|---|---|---|
| + | − | − | + | 68.9 ± 12.0 |

C: signal transduction inhibitors

| Inhibitor | Pre-incubation IGDS | Pre-incubation Inhibitor | In assay IGDS | In assay Inhib-body | % Inhibitor | Inhibitory activity yes(+) no(−) |
|---|---|---|---|---|---|---|
| Genistein (10 µg/ml) | − | − | + | + | 94.1 ± 6.5 | early events: + |
| | + | + | − | − | 96.7 ± 4.0 | late events: − |
| | + | − | − | + | 0.9 ± 2.9 | |
| PD98059 (2.0 µM) | − | − | + | + | 99.8 ± 3.8 | early events: + |
| | + | + | − | − | 90.5 ± 3.1 | late events: + |
| | + | − | − | + | 39.4 ± 5.0 | |
| PKA inhib (5 nM) | − | − | + | + | 90.0 ± 6.4 | early events: − |
| | + | + | − | − | 6.9 ± 5.7 | late events: + |
| | + | − | − | + | 99.5 ± 4.2 | |

TABLE 4

Angiogenic Activities of Synthetic Peptides and Gelatin-binding Domain of Fibronectin. The angiogenic activities of the indicated test compounds were ascertained in the chick yolk sac assay, as previously described in Gush et al (1990) J. Med. Engineer. Tech. 14, 205–209. See Legend FIG. 7 for further details.
Angiogenic Activity

| Compound | Concentration (ng/pellet) | Positive responses (%) |
|---|---|---|
| Control | — | 2/28 (7) |
| IGDS | 5 | 3/6 (50) |
| | 50 | 7/11 (64) |
| | 250 | 10/13 (77) |
| | 1000 | 9/14 (64) |
| | 3000 | 7/9 (78) |
| Gelatin-binding domain | 5 | 0/4 (0) |
| | 50 | 3/10 (30) |
| | 250 | 7/8 (87) |
| | 1000 | 9/12 (75) |
| | 3000 | 6/6 (100) |
| RGDS | 3000 | 1/11 (9) |
| RGES | 3000 | 1/10 (10) |

REFERENCES

The following references are hereby incorporated by reference.

1. Zardi, L. et al (1985) Eur. J. Biochem. 146, 571–579.
2. Postlethwaite, A. E. et al (1981) J. Exp. Med. 153, 494–499.
3. Albini, A. et al (1987) J. Cell. Biol. 105, 1867–1872.
4. Akiyama, S. K. & Yamada, K. M. (1985) J. Biol. Chem. 260, 10402–10405.
5. Clark, R. A. F. et al (1988) J. Biol. Chem. 263, 12115–12123.
6. Schor, S. L. (1980) J. Cell Sci. 41, 159–175.
7. Schor, S. L. et al (1996) J. Cell Sci. 109, 2581–2590.
8. Hynes, R. O. (1990) Fibronectins pp 132–135, Springer-Verlag: New York.
9. Main, A. L. et al (1992) Cell. 71, 671–678.
10. Aota, S. et al (1994) J. Biol. Chem. 269, 24756–24761.
11. Roekel, D. & Krieg, T. (1994) Exp. Cell Res. 211, 42–48.
12. Xu, J. & Clark, R. A. F. (1997) J. Cell Biol. 136, 473–483.
13. Fukai, F. et al (1993) Biochem. 32, 5746–5751.
14. Fukai, F. et al (1995) Biochem. 34, 11453–11459.
15. Gailit, J. & Clark, R. A. F. (1996) J. Cell Biol. 106, 102–108.
16. Yamada, K. M. et al (1990) Cancer Res. 50, 4485–4496.
17. Yamada, K. M. (1991) J. Biol. Chem. 266, 12809–12812.
18. Tooney, P. A. (1993) Immunol. Cell Biol. 71, 131–139.
19. Davis, G. E. (1992) Biochem. Biophys. Res. Commun. 182, 1025–1031.
20. Chan, B. M. et al (1992) Cell. 68, 1051–1060.
21. Schwartz, M. A. et al (1995) Annu. Rev. Cell Dev. Biol. 11, 549–599.
22. Palecek, S. P. et al (1997) Nature 385, 537–540.
23. Richardson, A. & Parson, J. T. (1995) BioEssays 17, 229–236.
24. Chen, Q. et al (1994) J. Biol. Chem. 269, 26602–26605.
25. Chernousov, M. A. et al (1991) J. Biol. Chem. 266, 10851–10858.
26. Humphries, M. J. et al (1994) Exp. Opin. Ther. Patents 4, 227–235.
27. Pierschbacher, M. D. et al (1994) J. Cell Biochem. 56, 150–154.
28. Yamada, K. M. & Kennedy, D. W. (1985) J. Cell Biochem. 28, 99–104.
29. Pierschbacher, M. D. & Ruoslahti, E. (1987) J. Biol. Chem. 262, 17294–17298.
30. Hunt, T. K. Wound Healing and Infection: Theory and Surgical Practice Appleton-Century-Crofts: New York (1980).
31. Britsch, S., Christ, B. & Jacob, H. J. "The influence of cell-matrix interactions on the development of quail chorioallantoic vascular system" Anal. Embryol. 180, 479–484.

The invention claimed is:

1. A composition comprising a compound consisting of a sequence selected from the group consisting of Ile-Gly-Asp (IGD) (SEQ ID NO:1), Ile-Gly-Asp-Ser (IGDS) (SEQ ID NO:2), Ile-Gly-Asp-Gln (IGDQ) (SEQ ID NO:3), and a non-peptide or peptide mimic thereof,
wherein the compound has cell migration increasing activity;
wherein if the sequence is a peptide mimic,
the Ile is replaced with an amino acid selected from the group consisting of Val, Leu, Phe, Trp, and Tyr; or
the Asp is replaced with Glu, or
the Gly is replaced with Ala.

2. The composition according to claim 1, wherein the sequence is a peptide mimic and wherein the Ile is replaced with an amino acid selected from the group consisting of Val, Leu, Phe, Trp, and Tyr.

3. The composition according to claim 1, wherein the sequence is a peptide mimic and wherein the Asp is replaced with Glu, or wherein the Gly is replaced with Ala.

4. The composition according to claim 1 wherein the amino acids isoleucine (I), glycine (G), aspartic acid (D), serine (S), glutamine (Q), valine (V), leucine (L), phenylalanine (F), tryptophan (W), tyrosine (Y), glutamic acid (E), or alanine (A) within the compound are in the L-configuration.

5. A pharmaceutical composition comprising the compound according to claim 1 and a pharmaceutically acceptable carrier.

6. A method of modulating cell migration, the method comprising administering to the site where cell migration is desired a therapeutically effective amount of a compound with a relative molecular mass of less than 15,000 comprising the peptide Ile-Gly-Asp (IGD) (SEQ ID NO:1) or a non-peptide or peptide mimic thereof with cell migration increasing activity,
wherein if the sequence is a peptide mimic,
the Ile is replaced with an amino acid selected from the group consisting of Val, Leu Phe, Trp, and Tyr, or
the Asp is replaced with Glu, or
the Gly is replaced with Ala.

7. The method according to claim 6, wherein the compound is a peptide mimic and
wherein the Ile is replaced with an amino acid selected from the group consisting of Val, Leu, Phe, Trp, and Tyr, or
wherein the Asp is replaced with Glu, or
wherein the Gly is replaced with Ala.

8. The method according to claim 6 wherein the cell is a fibroblast.

9. The method according to claim 6 wherein the cell migration site is in an animal body.

10. The method according to claim 6 wherein the cell migration site is in a mammalian body.

11. The method according to claim 8 wherein the cell migration site is in a human body.

12. The method according to claim 6 for increasing cell migration.

13. A compound with cell migration increasing activity and a molecular mass of less than 15,000 comprising a plurality of sequences selected from the group consisting of Ile-Gly-Asp (IGD) (SEQ ID NO:1), Ile-Gly-Asp-Ser (IGDS) (SEQ ID NO:2), Ile-Gly-Asp-Gln (IGDQ) (SEQ ID NO:3), and a non-peptide or peptide mimic thereof,
wherein if the sequence is a peptide mimic,
the Ile is replaced with an amino acid selected from the group consisting of Val, Leu, Phe, Trp, and Tyr; or
the Asp is replaced with Glu, or
the Gly is replaced with Ala.

14. The composition of claim 2, wherein the Ile in the peptide mimic is replaced with an amino acid selected from the group consisting of Val, Leu, Phe, and Tyr.

15. The composition of claim 2, wherein the Ile in the peptide mimic is replaced with an amino acid selected from the group consisting of Val and Leu.

16. A composition comprising a compound consisting of a sequence selected from the group consisting of Ile-Gly-Asp (IGD) (SEQ ID NO:1), Ile-Gly-Asp-Ser (IGDS) (SEQ ID NO:2), Ile-Gly-Asp-Gln (IGDQ) (SEQ ID NO:3), and a non-peptide or peptide mimic thereof,
wherein the compound has cell migration increasing activity; and
wherein if the sequence is a peptide mimetic;
the Asp is replaced with Glu, or
the Gly is replaced with Ala.

17. A composition with cell migration increasing activity and a molecular mass of less than 15,000 comprising more than one compound selected from the group consisting of Ile-Gly-Asp (IGD) (SEQ ID NO:1), Ile-Gly-Asp-Ser (IGDS) (SEQ ID NO:2), Ile-Gly-Asp-Gln (IGDQ) (SEQ ID NO:3), a non-peptide and peptide mimic thereof, wherein the compound has cell migration increasing activity,
wherein if the sequence is a peptide mimic,
the Ile is replaced with an amino acid selected from the group consisting of Val, Leu, Phe, Trp, and Tyr, or
the Asp is replaced with Glu, or
the Gly is replaced with Ala.

18. The peptide of claim 13, wherein the compound comprises a plurality of sequence Ile-Gly-Asp (IGD) (SEQ ID NO:1).

* * * * *